US006816564B2

(12) United States Patent
Charles, Jr. et al.

(10) Patent No.: US 6,816,564 B2
(45) Date of Patent: Nov. 9, 2004

(54) TECHNIQUES FOR DERIVING TISSUE STRUCTURE FROM MULTIPLE PROJECTION DUAL-ENERGY X-RAY ABSORPTIOMETRY

(75) Inventors: Harry K. Charles, Jr., Laurel, MD (US); Thomas J. Beck, Baltimore, MD (US); Howard S. Feldmesser, Columbia, MD (US); Thomas C. Magee, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/415,809
(22) PCT Filed: Nov. 8, 2001
(86) PCT No.: PCT/US01/47031
§ 371 (c)(1), (2), (4) Date: Oct. 21, 2003
(87) PCT Pub. No.: WO02/38045
PCT Pub. Date: May 16, 2002

(65) Prior Publication Data
US 2004/0077088 A1 Apr. 22, 2004

Related U.S. Application Data
(60) Provisional application No. 60/246,679, filed on Nov. 8, 2000.
(51) Int. Cl.⁷ .................................................. A61B 6/03
(52) U.S. Cl. ........................ 378/5; 378/18; 378/901
(58) Field of Search ........................... 378/4, 5, 8, 9, 378/15, 18, 19, 901

(56) References Cited
U.S. PATENT DOCUMENTS

| | | | |
|---|---|---|---|
| 4,417,353 A | 11/1983 | Groh et al. ............... | 328/4 |
| RE34,511 E | * 1/1994 | O'Neill et al. ............... | 600/425 |
| 5,432,834 A | 7/1995 | Gershman ................... | 378/196 |
| 5,661,774 A | 8/1997 | Gordon et al. .............. | 378/101 |
| 5,748,705 A | 5/1998 | Stein et al. ................. | 378/196 |
| 5,762,608 A | 6/1998 | Warne et al. | |
| 5,796,802 A | 8/1998 | Gordon ......................... | 378/8 |
| 5,838,765 A | 11/1998 | Gershman et al. .......... | 378/196 |
| 6,233,473 B1 * | 5/2001 | Shepherd et al. ........... | 600/407 |
| 2004/0028181 A1 * | 2/2004 | Charles, Jr. et al. .......... | 378/92 |

FOREIGN PATENT DOCUMENTS

EP   1 044 649 A1   4/2000

* cited by examiner

Primary Examiner—David V Bruce
(74) Attorney, Agent, or Firm—Francis A. Cooch

(57) ABSTRACT

Techniques for deriving bone properties from images generated by a dual-energy x-ray absorptiometry apparatus include receiving first image data having pixels indicating bone mineral density projected at a first angle of a plurality of projection angles. Second image data and third image data are also received. The second image data indicates bone mineral density projected at a different second angle. The third image data indicates bone mineral density projected at a third angle. The third angle is different from the first angle and the second angle. Principal moments of inertia for a bone in the subject are computed based on the first image data, the second image data and the third image data. The techniques allow high-precision, high-resolution dual-energy x-ray attenuation images to be used for computing principal moments of inertia and strength moduli of individual bones, plus risk of injury and changes in risk of injury to a patient.

78 Claims, 19 Drawing Sheets

MUSCLE DENSITY IMAGE

BONE MINERAL DENSITY IMAGE

TECHNIQUES FOR DERIVING TISSUE STRUCTURE FROM MULTIPLE PROJECTION DUAL-ENERGY X-RAY ABSORPTIOMETRY

CROSS-REFERENCE TO RELATED APPLICATIONS

This application claims the benefit of U.S. provisional application No. 60/246,679, filed on Nov. 8, 2000, which is hereby incorporated by reference in its entirety.

STATEMENT OF GOVERNMENTAL INTEREST

This invention was made with Government support under Cooperative Agreement NCC9-58-0 between the National Aeronautics and Space Administration (NASA) Johnson Space Center, Houston, Tex. and the National Space Biomedical Research Institute (NSBRI). The Government has certain rights in the invention.

BACKGROUND OF THE INVENTION

1. Field of the Invention

The present invention relates to dual-energy x-ray absorptiometry for tissue properties; and, in particular to techniques for deriving bone structure, bone strength, and risk of injury, including risk of fracture, from multiple projection dual-energy x-ray absorptiometry images.

2. Description of the Related Art

The system of bones and skeletal muscles provides structure to a human or animal body, and provides the capability to carry out activities. Bone provides the basic structural integrity of the body that carries forces and furnishes a framework for muscle.

Experience with bed rest subjects, astronauts and cosmonauts indicates that the magnitudes and patterns of bone tissue loss are extremely variable from one individual to the next, and also between different body regions. Little mass appears to be lost from the upper extremities during weightlessness; whereas the rate of mass loss from the vertebrae, pelvis, and proximal femurs of astronauts average between 1 percent and 1.6 percent per month. The rate of mass loss from those sites in postmenopausal woman average between 0.8 percent and 1.3 percent per year—a substantially lower rate of loss.

Recent evidence shows that there are important differences between the ways that bone is lost in aging on earth compared to changes observed during space flight. On earth, the skeleton is continually loaded during normal activities. Load causes mechanical strains within the bone, which tend to be greatest on the subperiosteal surface, the connective tissue with bone forming cells attached to the surface (cortex) of the bone. In response, more new bone mass forms on the cortex. Simultaneously, the normal turnover of bone accompanying the aging process causes some net loss of bone from endocortical (inside the cortex) and internal surfaces. In long bones, the net loss under loading causes skeletal strains to increase most on the subperiosteal surface, not at the internal surfaces where the bone loss occurred. Because it takes less new bone on the subperiosteal surface to compensate for bone loss from internal surfaces, strength can be maintained in the presence of net bone loss.

During space flight, loading is practically absent on the lower skeleton. Not only does bone loss accelerate under diminishing loading, but evidence from cosmonaut data suggests that the compensatory changes are absent as well. This means that astronauts may be at a greater risk of fracture for the same loss of bone mass. Therefore it is important not only to determine bone mass, but also to determine the geometrical configuration of the bone structure. Bones loss countermeasures can be developed to increase the loading on the lower skeleton. The efficacy of such countermeasures is better determined individually, based on the geometrical configuration of the individual's bone structure before and after the countermeasures, than by analyzing bone breakage statistics over a large population of astronauts. There is simply not a large population of astronauts.

Furthermore, the determination of bone structure is useful for screening a population and monitoring treatments of osteoporosis in postmenopausal women, elderly men and other susceptible individuals.

Loading and bone loss countermeasures can also be assessed through the measurements of muscle mass in a living human. Therefore it an advantage for a scanning device to also distinguish fat from muscle in soft tissue. Soft tissue excludes bone tissue.

There are several methods for determining bone mineral density (BMD), bone structure, and soft tissue components. These methods include computed tomography (CT), magnetic resonance imaging (MRI), ultrasound, and dual-energy x-ray absorptiometry (DXA).

While a CT unit can image and measure the geometrical characteristics of bone and soft tissue, it is not well suited for use in space because of its high radiation dose per scan. In addition, a CT unit capable of performing total body scans is extremely massive, weighing thousands of pounds. This great weight renders such units impractical for portable and space flight use. In addition, the high cost and large size place such units beyond the reach of small earthbound clinics, which might otherwise administer osteoporosis screening and treatment monitoring. An MRI unit is excellent for imaging soft tissues, for example to distinguish fat from muscle. However, an MRI unit suffers from a similar size and weight disadvantage. An MRI unit capable of performing whole body scans consumes significant power, generates large magnetic fields, and weighs tens of thousands of pounds.

Commercial scanners use dual-energy x-ray absorptiometry (DXA) or ultrasound to yield measurements of bone mineral density (BMD) that are regional averages. However, regional averages obscure structural details, and thus are not precise enough to deduce bone strength. Such systems do not predict risk of breakage. Furthermore, ultrasound devices have not been used successfully for the quantification of muscle mass.

In addition, commercial DXA devices consume too much energy for portable use. Furthermore DXA scanners employ ionizing radiation, which can pose a radiation risk to astronauts confined to operate in small spaces in the vicinity of a DXA device.

Based on the foregoing description, there is a clear need for techniques to derive bone structure, fat tissue mass and lean tissue mass from multiple projection, DXA systems.

Furthermore, there is a need for a system that yields a risk of injury including bone breakage.

SUMMARY OF THE INVENTION

According to one aspect of the invention, techniques for calibrating bone properties from dual-energy x-ray absorptiometry images, include receiving first image data and second image data. The first image data has pixels indicating attenuation through multiple known thicknesses of a first two calibration materials at a first photon energy. The second image data has pixels indicating attenuation through the multiple known thicknesses of the first two calibration materials at a second photon energy. A first conic-surface function and a second conic-surface function are determined. The first conic-surface function relates attenuation data from the first image data to the plurality of known thicknesses. The second conic-surface function relates attenuation data from the second image data to the plurality of known thicknesses. The first and second conic-surface functions are inverted to determine a pair of thickness functions. Each thickness function relates thickness of one calibration material to attenuations from the first image data and the second image data. The pair of thickness functions are applied with attenuations from image data comprising pixels indicating attenuation through tissue of a subject.

According to another aspect of the invention, techniques are provided for deriving bone properties from images generated by a dual-energy x-ray absorptiometry apparatus. The apparatus has an x-ray source in fixed relation to an x-ray receiver. The source and the receiver are moveably mounted to measure attenuation through a subject at multiple projection angles. First image data and second image data are received. The first image data has pixels indicating bone mineral density projected at a first angle of the multiple projection angles. The second image data has pixels indicating bone mineral density projected at a different second angle. Based on the first image data and the second image data, a magnification factor is computed. The magnification factor relates distances associated with pixels in the first and second image data to corresponding distances at a bone in the subject.

According to another aspect of the invention, techniques for deriving bone properties from images generated by the dual-energy x-ray absorptiometry apparatus includes receiving first, second, third and fourth image data. The first image data has pixels indicating attenuation of a first photon energy projected at a first angle. The second image data has pixels indicating attenuation of a second photon energy projected at the first angle. The third image data has pixels indicating attenuation of the first photon energy projected at a different second angle. The fourth image data has pixels indicating attenuation of the second photon energy projected at the second angle. A value indicating a bone mineral density for a particular pixel in the first image data is computed based on the first, the second, the third and the fourth image data.

According to an embodiment of this aspect, the step of computing the value indicating the bone mineral density includes determining a soft tissue composition for the particular pixel based on a set of pixels without measurable bone mineral density at the second angle. The value of the bone mineral density is determined based on the attenuation at the particular pixel in the first image data, the attenuation at a corresponding pixel in the second image data, and the soft tissue composition for the particular pixel.

According to another aspect of the invention, techniques for deriving bone properties from images generated by a dual-energy x-ray absorptiometry apparatus includes receiving image data having pixels indicating bone mineral density projected at a first angle. A long axis for a bone in the image data is determined. A first set of pixels is selected in the image data. The first set of pixels lie substantially along a line segment crossing the bone and perpendicular to the long axis. A cross sectional moment of inertia is computed for the bone based on the first set of pixels.

According to another aspect of the invention, techniques for deriving bone properties from images generated by a dual-energy x-ray absorptiometry apparatus includes receiving first image data, second image data and third image data. The first image data includes pixels indicating bone mineral density projected at a first angle. The second image data includes pixels indicating bone mineral density projected at a different second angle. The third image data includes pixels indicating bone mineral density projected at a third angle different from the first angle and the second angle. Principal moments of inertia for a bone in the subject are computed based on the first, the second and the third image data.

According to another aspect of the invention, techniques for deriving bone properties from images generated by a dual-energy x-ray absorptiometry apparatus includes receiving data indicating multiple principal moments of inertia for a bone in the subject. The data is based on images taken at several projection angles. A stress on the bone associated with a particular scenario is determined. A probability of the particular scenario is determined. A risk of injury is determined based on the probability of the particular scenario, the stress associated with the particular scenario, and the moments of inertia. The risk of injury is reported to a human operator.

These techniques allow derivations of bone and muscle strength, risk of injury, and efficacy of countermeasures among other properties, from high-precision bone structure measurements.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

Techniques for deriving bone properties from a multiple-projection, dual-energy x-ray absorptiometry apparatus are described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

1. Structural Overview

Figure 1A:
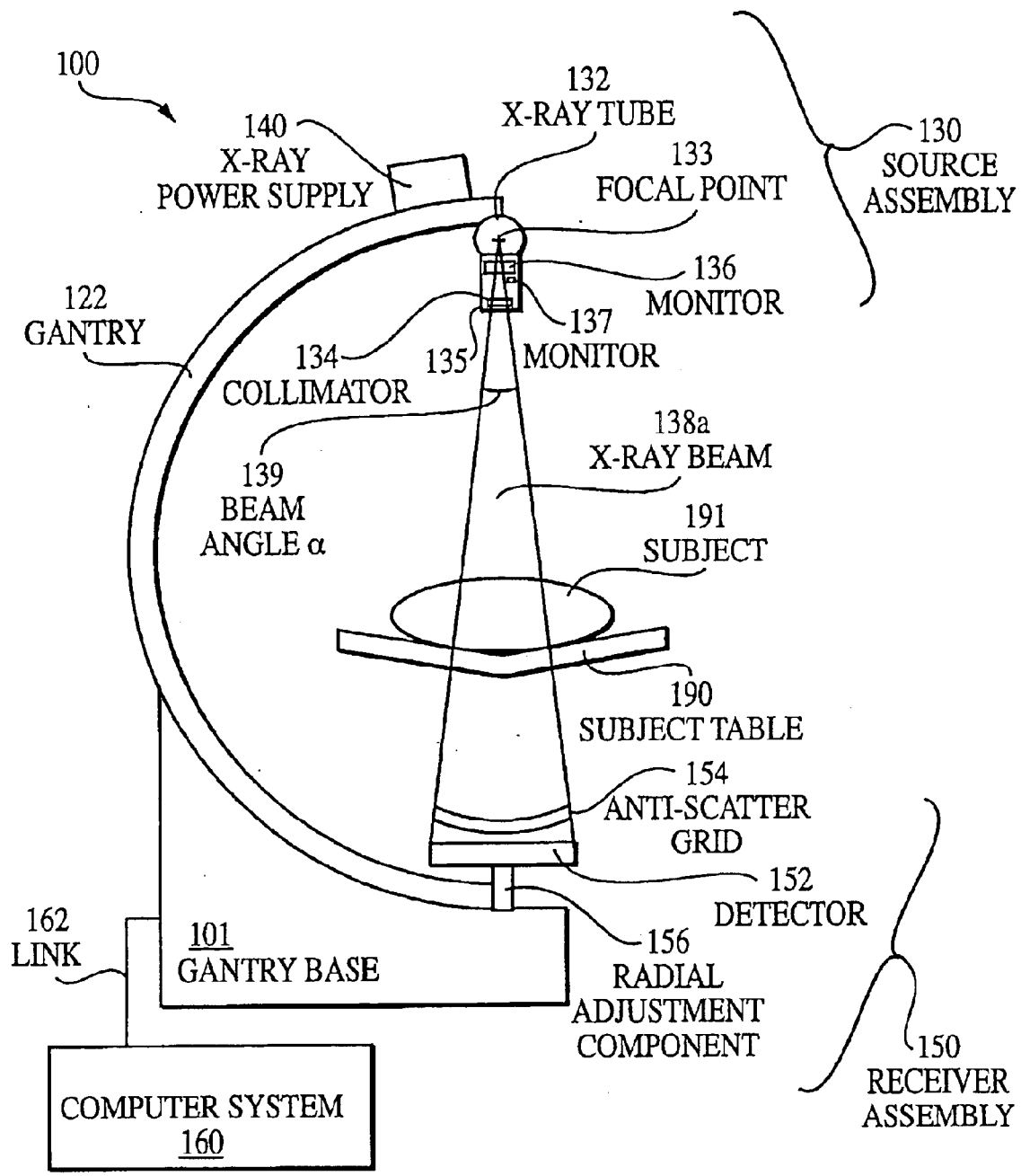
FIG. 1A is a block diagram illustrating structural components of an apparatus for multiple-projection, dual-energy x-ray absorptiometry, according to an embodiment.

FIG. 1A is a block diagram illustrating structural components of an apparatus 100 for multiple-projection, dual-energy x-ray absorptiometry, according to an embodiment. The cross section of FIG. 1A defines an X-Z plane in which Z is the vertical dimension and X is the horizontal dimension. A horizontal dimension extending out of the page, perpendicular to the X-Z plane, is the Y dimension.

The apparatus includes a gantry 122 shaped to hold an x-ray source assembly 130 in fixed relation to a receiver assembly 150. An x-ray beam 138a is emitted from the source assembly 130 to the receiver assembly 150. In an example embodiment, a centerline of the beam 138a lies in the X-Z plane. The gantry is moveably attached to a gantry base 101 so that the source assembly 130, the receiver assembly 150, and the beam 138a centerline rotate in the X-Z plane about an axis line in the Y dimension. The rotation preserves the distance and relative directions between the source assembly 130 and the receiver assembly 150. In other embodiments, the locations of the source assembly 130 and the receiver assembly 150 on the gantry are exchanged, so that the source lies below the subject and the receiver lies above. In other embodiments, the gantry has other shapes, such as an annular shape.

A subject table 190, transparent to x-rays, is disposed between the source assembly 130 and receiver assembly 150 in the X-Z plane. The subject table 190 supports a subject 191 during operation of the apparatus 100. Either the subject table 190 or the gantry base 101 or both are configured to translate in the Y dimension so that different portions of the subject 191 intersect the X-Z plane. In some embodiments, the subject table may also rotate in an X-Y plane about an axis line in the Z dimension. In other embodiments, the receiver assembly employs a detector large enough in the Y dimension so that the subject table is not translated in the Y direction.

The gantry is connected to a computer system 160 by a communications link 162. Through link 162, the computer system 160 controls the motion of the gantry 122 and gantry base 101, controls the operation of the source assembly 130, and receives data from a detector 152 of the receiver assembly 150. In some embodiments, the computer system also controls the movement of the subject table through link 162 or another link, not shown.

The source assembly 130 includes an x-ray power supply 140, an x-ray tube 132 and an x-ray beam-forming component 135. X-rays are electromagnetic waves. A discrete quantum of an electromagnetic wave is a photon. An x-ray with frequency (v) has a photon energy (E) proportional by Plank's constant h; that is, $E = h\, v$.

In the x-ray tube, high-energy electrons from a heated filament collide with a material (at a positively charged anode) where the electrons are suddenly decelerated to produce x-rays with a distribution (relative number of photons) per photon energy (frequency) determined by the energy of the incident electrons. A high voltage (V) input, V1, applied between the heated filament and the anode accelerates each electron before the electron slams into the anode. The kinetic energy of a single electron accelerated by a 1-volt electric field is an electron volt (about $1.6 \times 10^{-19}$ Joules, or $4.45 \times 10^{-24}$ kilowatt-hours). To produce x-rays, the voltage V1 is many tens of thousands of volts. The x-ray tube produces x-ray photons with a distribution of photon energies up to a cutoff photon energy determined by the input voltage V1; that is, all x-ray photons have energies less than or equal to a cutoff energy of V1 electron-volts (at cutoff frequency vc). The peak energy (at frequency vp) is the x-ray photon energy that has the most photons; the peak energy is slightly less than V1 electron-volts. The number of photons produced decreases with decreasing photon energy (frequency) below the peak energy (frequency vp).

The x-ray power supply 140 provides the high voltage input, V1, between the heated filament and the anode. The x-ray power supply 140 also provides enough electrons per second, current (I), to supply a useful number of electrons striking the anode. An Ampere of current is 1 coulomb per second, which is about $0.6 \times 10^{19}$ electrons per second. The power provided by the power supply is the product of the current I and the voltage V1. By definition, the unit of the product, an Ampere-volt, is a Joule per second, which by definition is 1 Watt.

In a dual-energy system, the power supply also drives the x-ray tube at a different voltage V2, which causes a different distribution of x-ray energies (frequencies) with a different cutoff energy (at a second cutoff frequency vc2) and a different peak energy (at a second peak frequency vp2).

The x-ray beam-forming component 135 includes a collimator 134 for shaping the beam angle 139 and a filter 136 for limiting the distribution of frequencies about the peak frequency. A monitor 137 is also included to measure x-ray characteristics of the source for changes that may affect calibration and for determining attenuation.

The collimator is made of an x-ray opaque material, such as lead, with an opening (aperture) size and shape selected to give the beam 138a a particular cross section in a plane perpendicular to the centerline. The beam angle α, in the X-Z plane across subject 191, may be different from the beam angle β, in the plane containing the centerline of the beam 138a and perpendicular to the X-Z plane, along subject 191.

The filter is made of a material that blocks the lower energy x-rays, below the peak energy, passing only x-rays with energies above a high-pass energy (at frequency va). As a result, only a narrow range of x-ray photon energies, from a high pass energy (at va) just below the peak energy (at vp) to the cutoff energy (at vc), emerges from the x-ray source assembly 130. In a dual-energy system, a second filter is used when the power supply drives the x-ray tube at the second voltage V2. The second filter blocks x-ray photon energies below a second high pass energy (at va2), which is less than the second peak energy (at vp2).

The receiver assembly 150 includes a detector 152, an optional radial adjustment component 156, and an anti-scatter element, such as anti-scatter grid 154. The detector includes one or more receptors that respond to the x-ray fluence (energy per unit area). The diminution of fluence from the source assembly to a receptor in the detector along any radial line is due to geometrical spreading of the beam, which is easily calculated, and the absorption by the subject 191 and subject table 190. The absorption by the subject depends on the photon energy (frequency) of the beam and the material in the subject 191.

The anti-scatter element reduces the number of photons striking the detector from directions other than a radial direction to the detector from a focal point 133 in the x-ray tube. The material in subject 191 and table 190 absorbs some x-ray photons and scatters some in other directions. If these scattered photons strike the detector, the measured intensity is increased and the computed attenuation is erroneously decreased. Estimates of scattering may be made to correct the computation of absorption, but the estimates are both difficult and imprecise. If the scattering can be reduced, both the speed and the precision of the absorption computation can be enhanced. The anti-scatter component is usually made up of an x-ray opaque material, such as lead, with slits aligned perpendicularly to the detector, so that only photons traveling on a perpendicular ray strike the detector 152. Such perpendicular slits eliminate much of the scattering in conventional DXA systems. In one embodiment, the anti-scatter grid includes holes arrayed over a spherically curved lead sheet large enough to cover the detector 152 and having a radius of curvature that matches the distance from the grid to a focal point 133 in the x-ray tube 132.

The radial adjustment component 156 allows the distance from the detector 152 to the subject 191 or focal point 133 or both to be changed. It is sometimes advantageous to change these distances. For example, decreasing the distance from subject 191 to detector 152, and increasing the radial distance from receiver assembly 150 to source assembly 130, may allow the entire subject to be imaged at one time. This is one way a full body scan of subject 191 is obtained. The system 100 would be re-calibrated whenever this distance is changed.

Figure 1B:
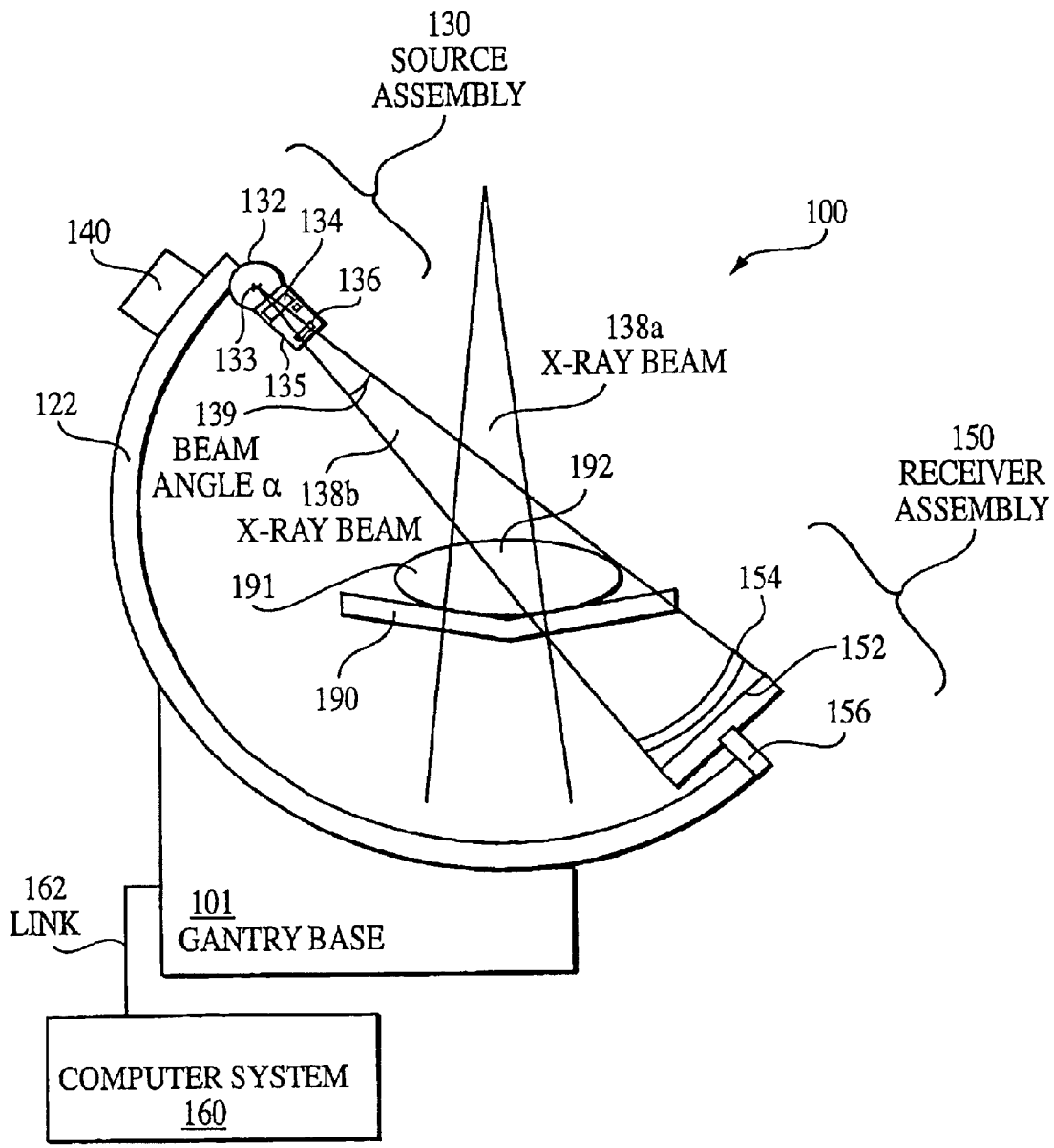
FIG. 1B is a block diagram illustrating the apparatus of FIG. 1A when configured for a different projection angle.

FIG. 1B is a block diagram illustrating the apparatus of FIG. 1A when configured for a different projection angle. In FIG. 1A the projection angle of the x-ray beam 138a from source assembly 130 to receiver assembly 150 is −90 degrees, as measured counterclockwise from a horizontal ray pointing to the right. The location of the −90 degree x-ray beam 138a is shown in FIG. 1B for reference. In the configuration of FIG. 1B, the gantry 122, with its fixed assemblies 130, 150, has been rotated 45 degrees counterclockwise by mechanisms in gantry base 101 under control of computer 160. In FIG. 1B the projection angle is −45 degrees. As a result, an x-ray beam 138b intersects a different portion of the subject 191. By rotating the gantry 122 45 degrees clockwise, another projection angle of −135 degrees, is obtained.

The portion 192 of subject 191 is illuminated by both beams 138a, 138b. Consequently data is obtained on bones in portion 192 of subject 191 for two projection angles, −90 degrees and −45 degrees.

According to embodiments of the invention, the properties of the structural elements in system 100 are selected to provide more spatially detailed measurements of absorption than are available from conventional dual-energy x-ray absorptiometry (DXA) systems. For example a high-resolution detector is employed and a three-dimensional anti-scatter grid 154 is employed. According to an embodiment, an advanced, multiple-projection, dual-energy x-ray absorptiometry (AMPDXA) scanning system is used. The AMPDXA includes a conical collimator; a high-resolution two-dimensional detector; a portable, power-capped, variable-exposure-time power supply; an exposure-time control element; calibration monitoring; a three-dimensional anti-scatter-grid; and a gantry-gantry base combination that permits up to seven projection angles for overlapping beams.

Figure 2A:
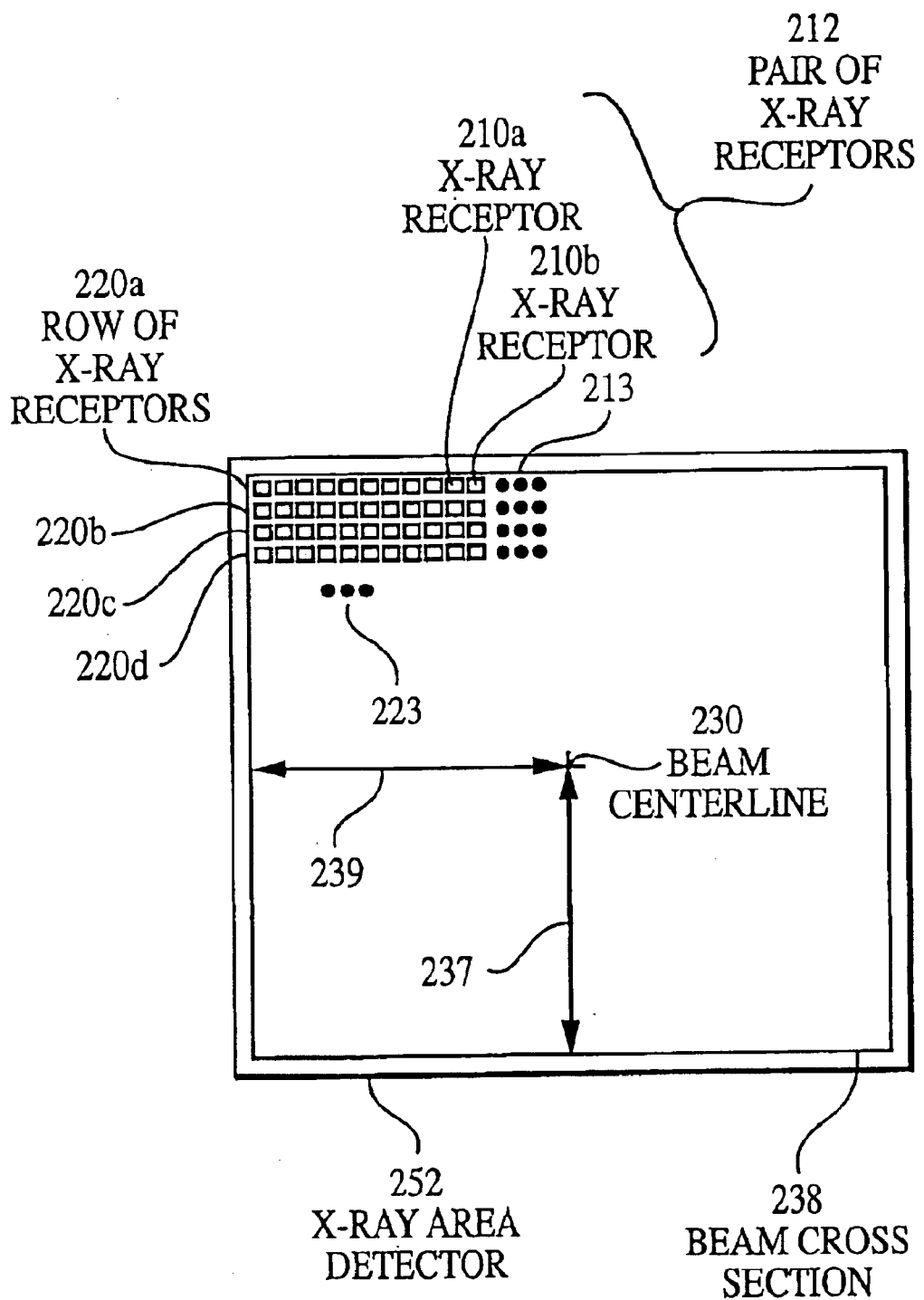
FIG. 2A is a block diagram illustrating an area detector for a dual-energy x-ray absorptiometry apparatus, according to an embodiment.

FIG. 2A is a block diagram illustrating an area detector 252 for a dual-energy x-ray absorptiometry apparatus, according to an embodiment of x-ray detector 152 in FIG. 1A. The area detector 252 has a length and width to substantially enclose the cross section (238) of the rectangular conical beam at the distance where the detector 252 is disposed in the receiver assembly (150 in FIG. 1A). The beam centerline intersects the detector at point 230. The width of the beam at the detector in the X-Z plane is indicated by double arrow 239 and the width of the beam at the detector in the perpendicular plane including the centerline is indicated by the double arrow 237.

The detector is configured with an array of receptors that respond to the fluence of impinging x-rays. Adjacent receptors distinguish fluence at adjacent locations. The highest resolution of the detector is determined by the size and separation of the pair of adjacent receptors, such as receptors 210a, 210b that constitute pair 212. The resolution is often expressed as the number of receptor pairs per millimeter (mm); the larger the number, the better the resolution.

Several detectors are known in the art. For example, many use scintillator materials, which produce visible light when struck by x-rays. The scintillator is coupled to an array of photodiodes. Conventional DXA systems use receptors arranged in one or two lines, with resolutions of 0.1 to 1 pairs per mm along each line. According to embodiments of the invention, detectors are used with resolutions of 2 or more pairs per millimeter. This provides improved resolution employed to produce structural models of bones that are not achievable with conventional DXA systems.

The receptors are arranged in rows. FIG. 2A shows a row 220a of receptors that includes several squares indicating receptors and ellipsis 213, which indicates additional receptors are included in the row. FIG. 2A shows rows 220a, 220b, 220c, 220d and ellipsis 223, which indicates additional rows of receptors are included in the detector. Conventional DXA systems use receptors arranged in one or two rows. According to the illustrated embodiment, the area detector 252 is filled with rows of receptors. By using an area detector that substantially encloses the conical beam, more of the photons produced by the x-ray tube are utilized in measuring absorption by the subject; therefore, less power is wasted. In addition, less time is consumed to scan the subject because each exposure of the illustrated system images an area that takes tens or hundreds of exposures using conventional DXA systems. Furthermore, less complex scanning mechanisms can be employed because scanning steps need not be precise steps less than a millimeter in size.

According to some embodiments of the invention, the properties of the structural elements in system 100 are selected to enhance portability of the system. For example, a smaller, more portable power supply than in the conventional DXA systems is used. The power supply is controlled by an exposure control system.

The noise level at the detector 152 is determined by the number of visible light photons (or free electrons) collected per pixel during data acquisition over the full exposure time. Noise decreases with an increase in the square root of the number of photons collected divided by the average number of photons per pixel over the whole detector. Noise is therefore inversely proportional to the detected fluence. To decrease the noise it is best to increase the fluence by increasing the number of pulses and hence the exposure time. However, signal is lost if the exposure time is increased so long that the dynamic range (difference between highest recordable intensity and lowest recordable intensity) is exceeded. To maximize the signal to noise ratio (SNR) at the detector, it is best to expose the detector to only enough pulses that the brightest pixels are about at the maximum recordable intensity value. A target fluence at the detector associated with an adequate SNR near the maximum SNR is determined during calibration.

An individual subject may often deviate significantly from the average subject. Absorption of x-rays increases exponentially with subject thickness. Therefore the fluence of x-rays at the detector decreases exponentially with subject thickness and the noise increases exponentially. These deviations are significant from one individual to the next. Thus, according to embodiments of the invention, exposure time, expressed in seconds or number of pulses, is adjusted based on the fluence of x-ray photons measured for the individual at the detector.

Figure 2B:
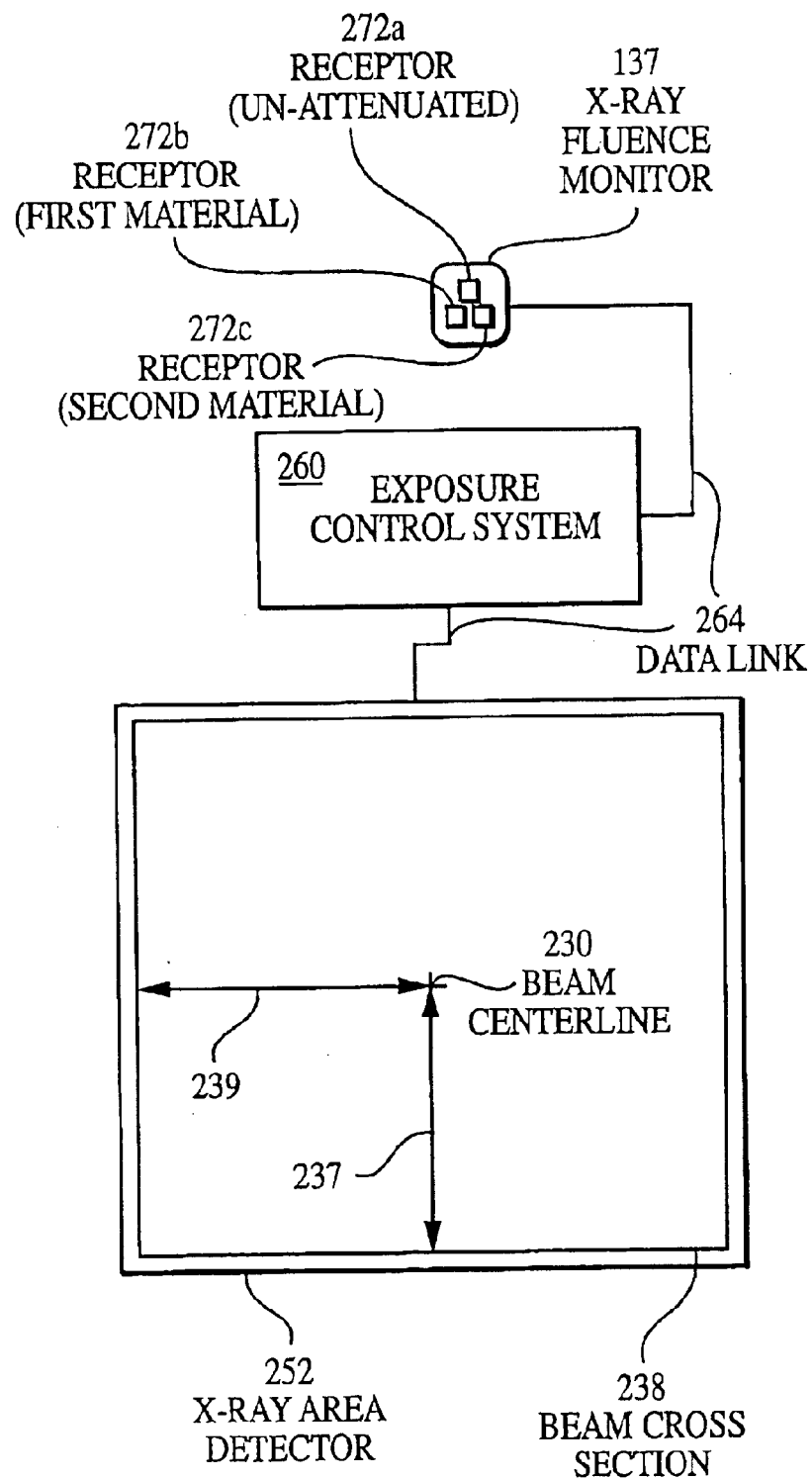
FIG. 2B is a block diagram illustrating a fluence detector that provides input to an exposure control system, according to an embodiment.

FIG. 2B is a block diagram illustrating a fluence detector that provides input to an exposure control system for the portable power supply, according to an embodiment. The exposure control system 260 is connected by a data link 264 with an x-ray area detector 252 and an x-ray fluence monitor 137. The use of the x-ray fluence monitor 137 is described in more detail in the next section with respect to monitoring calibration.

The beam centerline intersects the detector 252 at point 230. The width of the beam at the detector in the X-Z plane is indicated by double arrow 239 and the width of the beam at the detector in the perpendicular plane including the centerline is indicated by the double arrow 237. According to embodiments of the invention, the exposure control system 260 receives data from one or more receptors of the area detector 252 for each of one or a few pulses. The data are used as a test exposure to compute the fluence at detector 252 per pulse. The predetermined target fluence desired for the adequate SNR is divided by the computed fluence per pulse to determine the number of pulses and hence the exposure time.

In some embodiments, the exposure time (or the number of pulses) is computed based on an average attenuation and the x-ray fluence emerging from the source assembly. In such embodiments the x-ray fluence at the source is measured with a first receptor 272a in an x-ray fluence monitor 137 placed in the beam forming component. Attenuation is computed based on the ratio of the fluence at the source measured at receptor 272a and the fluence at the detector 252 using equation 1, described below. In some embodiments, the exposure control system 260 turns off the power supply when the computed number of pulses has been fired.

According to many embodiments, the intensity measured by the detector 252 at the end of the exposure includes the photons used in the test exposure. Thus the subject is not exposed to any extra radiation in order to determine the exposure time. The computation of bone mineral density at each pixel is determined based on the intensity images generated, as described in more detail below.

In addition, according to embodiments of the invention, the method of operating system 100 is modified to produce results that support the computation of structural strength of individual bones, unlike conventional DXA systems. For example, exposures at multiple projection angles are employed with overlapping beam volumes, and computer software is executed to form three-dimensional models of the bones, and to compute strength properties and risk of fracture based on the models. For another example, exposure time is controlled to maximize signal to noise ratio (SNR) using smaller, more portable power supplies.

In addition, according to an embodiment, the AMPDXA is configured to use a low photon energy beam at 80 kV and a high photon energy beam at 140 kV. In other embodiments, the low photon energy beam is separated even more from the high photon energy beam to better distinguish bone minerals from soft tissue. For example, in some embodiments the low photon energy beam is at 50 kV.

The gantry is configured to so that beams at multiple projection angles illuminate a particular volume in a subject. Three projections of the same bone are often adequate to form useful three dimensional (3-D) models. The use of three projection angles may not be adequate in cases where there are two bones in the volume, such as in the forearm and lower leg. Simulations indicate that five projections are adequate in those cases. Thus, in some embodiments, the gantry is configured to allow at least five intersecting beams at five projection angles. To model the hip, in some embodiments, the subject table is configured to rotate to image in a plane including the hip bone neck-shaft angle. In some embodiments, seven projection angles are used to model the hip bone.

The gantry is also configured to acquire a whole body bone mineral density image. In some embodiments this is accomplished by using a detector and beam width wide enough to sample the entire subject in the X-Z plane for at least some positions of the subject table.

2. Functional Overview

Figure 3:
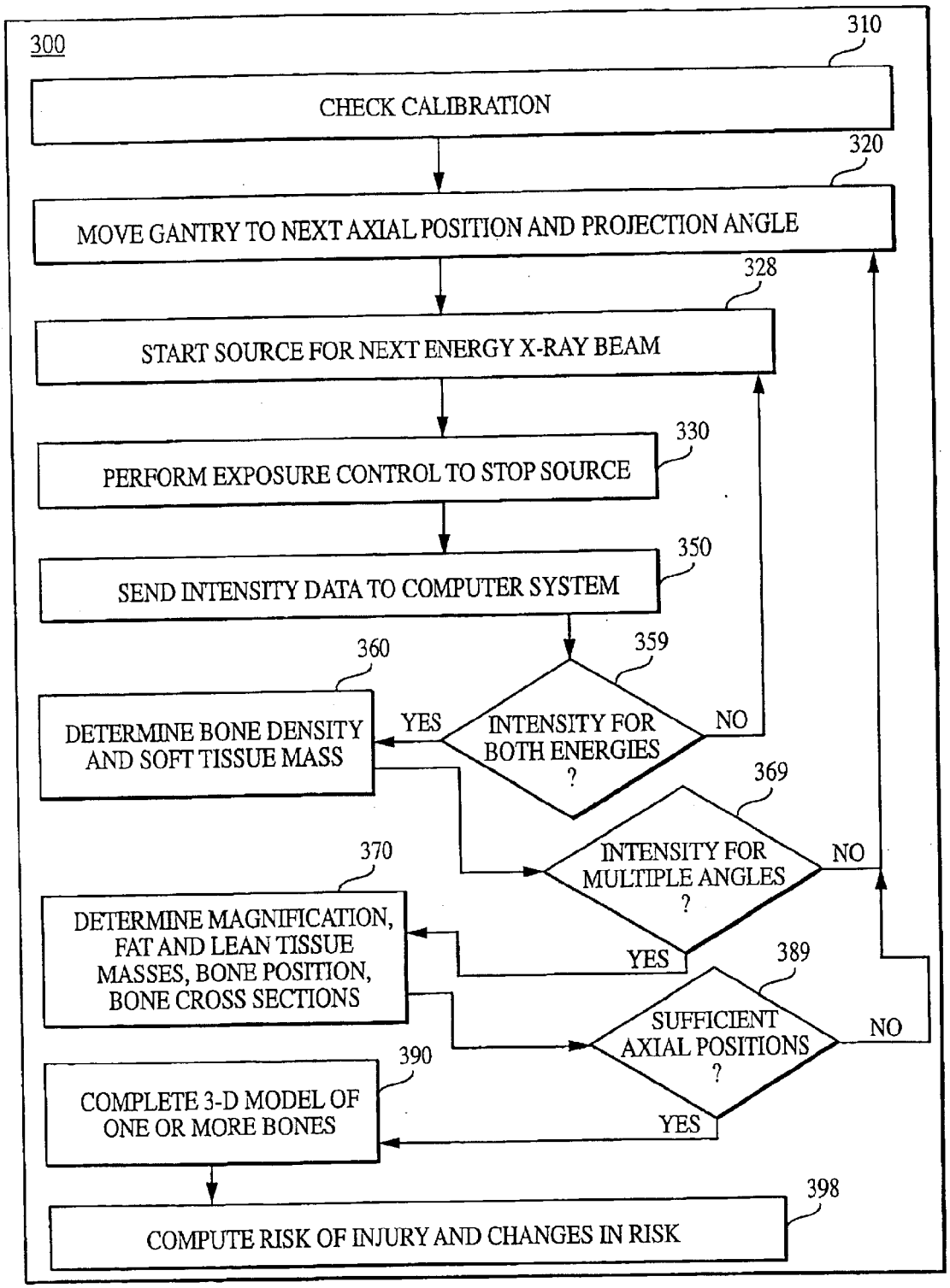
FIG. 3 is a flow chart illustrating at a high level a method for operating a multiple-projection dual-energy x-ray absorptiometry apparatus, according to an embodiment.

FIG. 3 is a flow chart illustrating at a high level a method 300 for operating a multiple-projection dual-energy x-ray absorptiometry apparatus, according to an embodiment. Although steps are shown in a particular order in FIG. 3 and following flow charts, in other embodiments the steps can be reordered or can overlap in time.

Figure 4A:
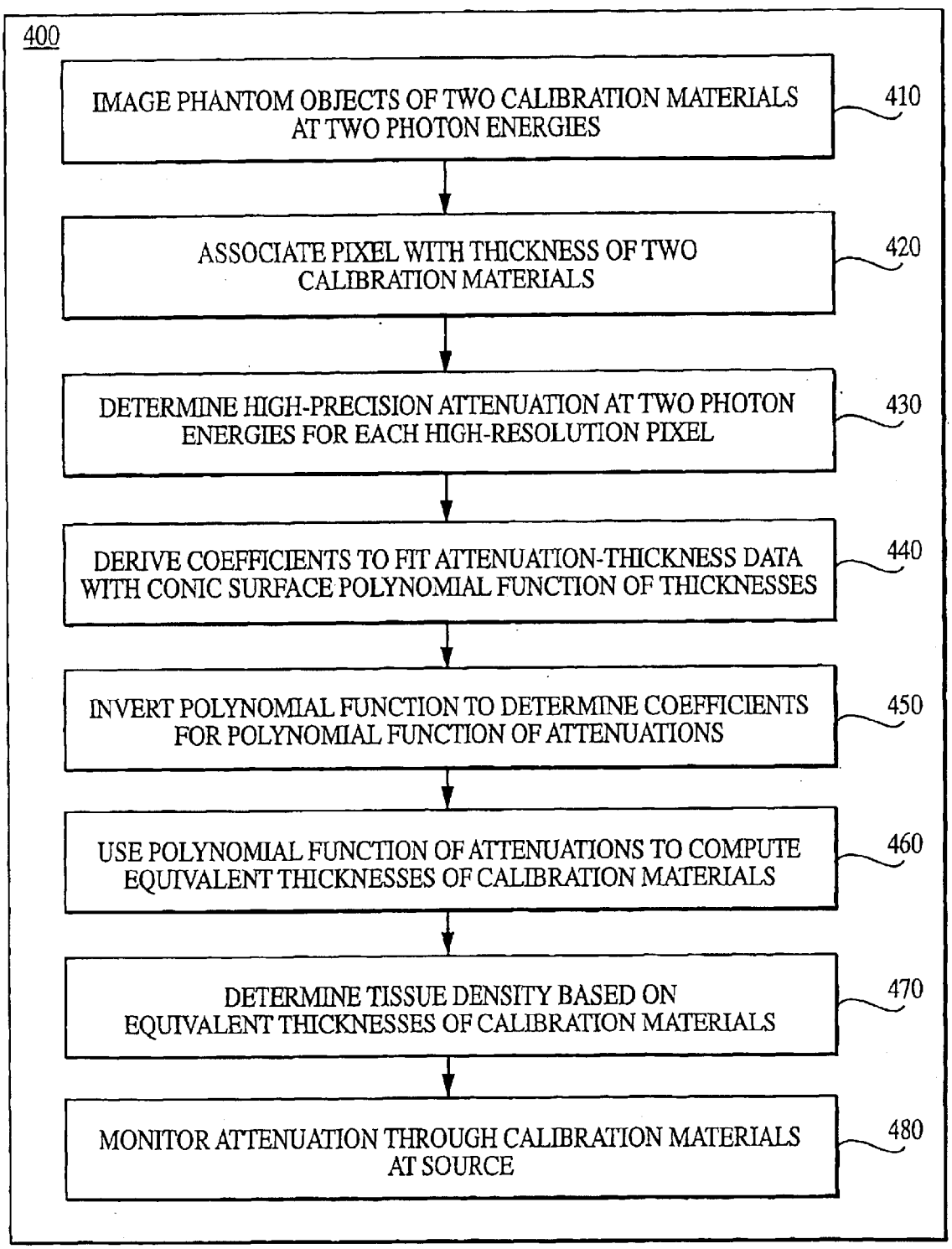
FIG. 4A is a flow cart illustrating details of a step of the flow chart of FIG. 3 for calibrating attenuation data, according to an embodiment.

In step 310, the calibration is determined. Calibration is described in more detail below with reference to FIG. 4A and FIG. 4B.

In step 320, the subject on the subject table and gantry are positioned to acquire an image at the next axial position and projection angle. For example, initially a patient subject 191 is positioned on the subject table 190 so that the long axis of a bone to be scanned is approximately aligned with the Y dimension and the region to be scanned is centered on the beam center intersection with the subject table 190. In some embodiments laser alignment devices are used. The patient limb is immobilized with a positioning device. The initial projection angle is also set. For example a projection angle of −90 degrees clockwise from horizontal is set. In some embodiments, step 320 includes moving the subject table toward the receiver assembly to obtain an image that encompasses the entire width of the subject as part of a whole body scan.

For example, if three projection angles are to be imaged, step 320 includes moving the gantry to a first projection angle of the three initially. In subsequent visits to step 320, the gantry is moved to a second or third projection angle of the three projection angles. If additional portions of the subject in the Y dimension are to be imaged, in a subsequent visit, the subject table or gantry is moved in the Y direction to the next position.

In step 328, the source for the next photon-energy beam is started. If no beam has yet been imposed on the subject, the next energy beam is one of the two or more photon energies. If a first photon-energy beam has been imposed on the subject, then another of the two or more photon-energy beams are started. For example, exposure control system 260 sends a signal to power supply 140 to form pulses at the driving voltages across x-ray tube 132.

In step 330, exposure control is performed to determine when to stop the source for the current beam. Step 330 is described below in more detail for one embodiment with reference to FIG. 5.

In step 350, intensity data is sent to computer system 160 to compute the attenuation image. In some embodiments step 350 includes computing attenuation for the current photon-energy beam. In other embodiments, the computation of attenuation is performed during step 360, described below.

In step 359, it is determined whether both photon energy beams have been imposed on the subject. If not, control passes to step 328 to start the source for the next photon-energy beam. If so, control passes to step 360 to determine bone mineral density and soft tissue mass at each pixel. Step 359 can be performed in any manner known in the art. For example, step 359 can be a branch point in a software program in one embodiment, a circuit switch in another embodiment, or a choice by a human operator in another embodiment.

In step 360, the two attenuations at the two photon-energies for each pixel and the calibration data are used to decompose two thicknesses for each pixel. For example, bone thickness and soft tissue thickness are computed. If no bone is available in the pixel, then, in some embodiments, thicknesses for fat and lean tissue are determined based on the two attenuations. In some embodiments, step 360 includes computing bone mineral density and soft tissue mass in units of mass per unit area (grams per square centimeter) based on the thickness and the known density of such tissue. In other embodiments, bone mineral density and soft tissue mass are computed in a later step. Step 360 is described in more detail below with respect to FIG. 4C, FIG. 4D and FIG. 4E.

In step 369, it is determined whether both photon-energy beams have been imposed on the subject at all projection angles. If not, control passes to step 320 to move the gantry to the next projection angle. If so, control passes to step 370 to determine tissue properties that can be deduced from multiple projection angles. Step 369 can be performed in any manner known in the art. The number of projection angles depends on operational choices for the particular bone being scanned. Three projections spanning at least 90 degrees angular separation are often sufficient. Where multiple bones appear in one or more of the first three projections additional projections are used, for example five projections are used. In difficult areas, such as the human hip, even more projections may be used.

In step 370 tissue properties deduced from multiple angles are computed. Step 370 is described in more detail below with reference to FIG. 6A, FIG. 6B and FIG. 6C.

In step 389, it is determined whether images have been obtained at a sufficient number of axial positions. If not, control passes to step 320 to move the gantry or subject table to obtain an image at the next axial position. If so, control passes to step 390 to determine tissue properties that can be deduced from multiple axial positions. Step 369 can be performed in any manner known in the art. The number of axial positions depends on operational choices for the particular bone being scanned. Often a single axial position suffices. For example, if the entire bone to be scanned appears in the image, no further axial positions are needed and control passes directly to step 390. In a whole body scan, for example, several axial positions are usually involved even if the area detector is large enough to image the entire width of the subject in the X-Z plane.

In step 390 tissue properties deduced from the one or more axial positions are computed. For example, principal moments of inertial for an entire bone can be derived. From the principal moments of inertia a three dimensional (3-D) model with patient specific mechanical properties is derived. Step 390 is described in more detail below with respect to FIG. 7. Control then passes to step 398.

In step 398, estimates of risk of injury; including risk of bone breakage are computed. For example, estimates of mechanical strength, scaled for body size, gender and other factors, are computed. In some embodiments, step 398 includes determining the spatial relationship between bones and metal objects implanted in the patient for repair or as prosthetics. Such spatial relationships may evidence separation and loosening of the metal objects at an early stage before complete failure. Step 398 is described in more detail below with reference to FIG. 8.

In some embodiments 3-D models and risk of injury are computed and stored at several different times that are days, weeks, months, or years apart. In such embodiments, differences in mechanical properties and risks of injury may be computed. In some embodiments, step 398 includes determining the efficacy of countermeasures for bone loss based on such changes in risk over time.

The 3-D modeling is expected to provide useful information for many additional applications besides bone strength. For example, the system can be used to construct the spatial relationship between bones and metal objects implanted in the patient for repair or as prosthetics. Such spatial relationships may evidence separation and loosening of the metal objects at an early stage before complete failure.

3. Methods for Deriving Bone Properties

According to embodiments of the invention, a software system executing on computer system 160 includes processes that perform 1) calibrating attenuation and tissue densities; 2) dynamically adjusting exposure; 3) deriving bone properties from multiple projection angles; 4) generating a three-dimensional (3-D) model; and, 5) determining risk of injury.

3.1 Calibration

DXA methods measure attenuation through a subject for each pixel in the image formed of the subject at the detector. Attenuation H is computed according to equation 1.

$$H = -\ln(Fs/F0) \qquad (1)$$

where ln is the natural logarithm function, Fs is the fluence at the pixel with the subject present and F0 is the fluence at the pixel without the subject present. These two values cannot be recorded simultaneously. In some approaches, the value of Fs is determined by making an exposure with the subject present and F0 is determined by making a similar exposure at a later time with the subject absent. However, the characteristics of the x-ray tube may not be identical at the two times. Beam characteristics are sensitive to small changes in the driving voltages that can often occur.

According to embodiments of the invention, the fluence monitor 137 placed in the beam-forming component 135 (FIG. 1A) determines F0 simultaneously with the measured quantity Fs. The fluence monitor 137 is located between the filter 136 and the collimator 134 so as not to block the aperture in the collimator. Fluence is recorded at that point over the same exposure time as is used to generate a fluence image at the detector 252. The fluence at the detector without the subject, F0, is then computed by computing the radial spreading of the x-ray beam from the distance of the fluence monitor to the distance of the detector.

For example, the intensity data corrected for flat-field, scatter and glare at each pixel is divided by the fluence data at fluence monitor 137 corrected for geometrical spreading to the flat detector, and the negative natural log of the result, according to Equation 1, is sent as an attenuation value for the pixel.

Attenuation at each pixel is transformed to thickness of tissue based on data collected with a calibration phantom. DXA methods are based on the assumption that x-ray images acquired at two photon-energies can be decomposed into equivalent images. Each equivalent image indicates the thickness of one of two known basis materials, herein called calibration materials. Calibration involves imaging of calibration phantoms each consisting of a set of orthogonal thicknesses of a two calibration materials. According to these methods, attenuation at each photon-energy is a polynomial function of the thicknesses of the two calibration materials. The coefficients of the polynomial are determined by measurements on the phantoms. The polynomial functions are inverted to yield the thickness of each calibration material as a polynomial function of the attenuations at the two photon-energies. This process is laid out in the flow chart of FIG. 4A.

In step 410, two phantom objects are aligned perpendicular to each other on the subject table and two attenuation images are produced, one at each x-ray photon energy. Results are acceptable, when the calibration materials have attenuations that differ at different photon energies in a way similar to the difference between the subject tissues, and when the range of thicknesses of the phantom objects correspond to the range of thicknesses of the tissues that are encountered in the subject. For example, aluminum or calcium phosphate tribasic type IV is used as a calibration material corresponding to bone, and acrylic (methyl methacrylate) or Plexiglas is used as a calibration material corresponding to soft tissue. A pixel including only soft tissue can be decomposed into fat and lean tissue using phantom objects made of 0.6% sodium chloride solution as a calibration material corresponding to lean tissue, and stearic acid as a calibration material corresponding to fat tissue.

Figure 4B:
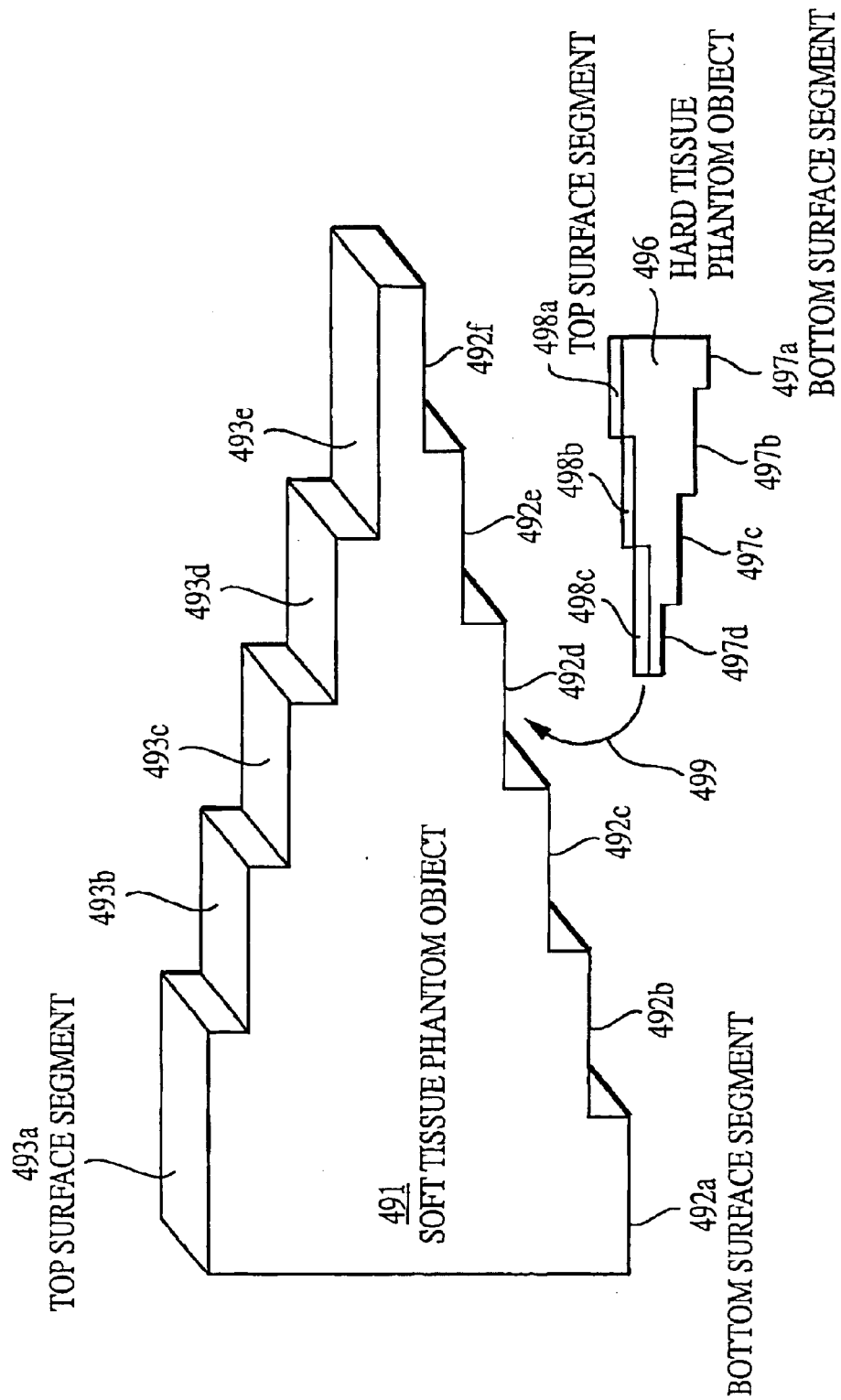
FIG. 4B is a block diagram illustrating two phantom objects used together as a subject to calibrate the x-ray absorption measurements and check the exposure control system, according to an embodiment.

FIG. 4B is a block diagram illustrating two phantom objects used together to calibrate the x-ray thickness measurements and check the exposure control system, according to an embodiment. In the illustrated embodiment, the soft tissue phantom object 491 includes 11 thicknesses of acrylic in 25.4 mm steps from 0 to 254 mm. The thicknesses occur between five top surface segments 493a, 493b, 493c, 493d, 493e (collectively called top surface 493) and six bottom surface segments 492a, 492b, 492c, 492d, 492e, 492f (collectively called bottom surface 492). The greatest thickness, 254 mm, occurs between bottom surface segment 492a and top surface segment 493a. The next greatest thickness occurs between the same top surface segment 493a and the next bottom surface segment 492b. The steps between segments on the bottom surface are staggered from the steps between segments on the top surface so that two thicknesses are associated with each surface segment (except 492a).

In the illustrated embodiment, the hard (bone) tissue phantom object 496 includes 7 thicknesses of aluminum in 5 mm steps from 0 to 30 mm. The thicknesses occur between three top surface segments 498a, 498b, 498c (collectively called top surface 498) and four bottom surface segments 497a, 497b, 497c, 497d (collectively called bottom surface 497). The greatest thickness, 30 mm, occurs between bottom surface segment 497a and top surface segment 498a. The next greatest thickness occurs between the same top surface segment 493a and the next bottom surface segment 497b. The steps between segments on the bottom surface are staggered from the steps between segments on the top surface so that two thicknesses are associated with each surface segment (except 497a).

The hard tissue phantom object 496 may be placed on one of the top or bottom surface segments of soft tissue phantom object 491, as indicated by arrow 499 to obtain calibration data for two acrylic thicknesses and 7 aluminum thicknesses (14 combinations) in one image. A total of 77 combinations of thicknesses can be obtained in seven images. Alternatively six copies of the hard tissue phantom can be generated, one each placed on six bottom surface segments, and the 77 combinations can be obtained in one image. The 77 combinations are used to deduce coefficients relating attenuations at two photon-energies to thicknesses of two calibration materials.

In other embodiments, a soft tissue phantom object comprises five thicknesses of plastic from 50 mm to 250 mm in increments of 50 mm, and a bone tissue phantom object comprises five thicknesses of aluminum of about 1.5 mm, 6 mm, 13 mm, 19 mm, and 38 mm. In other embodiments, phantoms of several thicknesses are generated as analogs for fat and muscle tissue.

In step 420, each pixel is associated with a pixel set for which the thickness of the first calibration material and the thickness of the second calibration material are both constant. In step 430 the attenuation is determined for both photon energies at all pixels. The attenuation is a high precision measurement not available from conventional DXA systems because of the use of the fluence monitor and the anti-scatter grid. The attenuation is also a high resolution measurement that is not available from conventional DXA systems because the area detector has two or more receptors per millimeter. As a result of steps 420 and 430 each combination of calibration materials thicknesses is associated with attenuations at two photon energies for all the pixels in the pixel set. The calibration data consists of all the attenuations measured for all the pixels for each pixel set and the associated thicknesses of the calibration materials.

In step 440 coefficients are derived by fitting a thickness function to the calibration data. For example, in one embodiment a pair of second order polynomial functions of thickness are fit to the data, one at each photon energy, as given by equations 2a and 2b.

$$HL = k1*T1 + k2*T2 + k3*T1^2 + k4*T2^2 + k5*T1*T2 \quad (2a)$$

$$HH = k6*T1 + k7*T2 + k8*T1^2 + k9*T2^2 + k10*T1*T2 \quad (2a)$$

where HL and HH are the attenuations at the low and high x-ray photon energies, respectively, and T1 and T2 are the thicknesses of the two calibration materials. The coefficients k1 through k10 are determined to give fit to the data, using techniques well known in the art of data fitting, such as a least squares fit. In another embodiment, conic-surface equations are used as the function fit to the data.

In step 450 pair of functions are inverted to determine the coefficients of a pair of functions of attenuation. For example the equations 2a and 2b are inverted to yield equations 3a and 3b.

$$T1 = q1*HL + q2*HH + q3*HL^2 + q4*HH^2 + q5*HL*HH \quad (3a)$$

$$T2 = q6*HL + q7*HH + q8*HL^2 + q9*HH^2 + q10*HL*HH \quad (3b)$$

where coefficients q1 through q10 depend on coefficients k1 through k10 algebraically. In other embodiments the conic-surface functions are inverted. In some embodiments, the data are fit to the pair of functions of attenuation directly; and step 450, to invert the functions, is omitted. For example, the coefficients q1 through q10 are determined by fitting the calibration data to equations 3a and 3b.

In step 460, the functions of attenuation are used with attenuation measurements on tissue samples of known thickness to compute equivalent thicknesses of the calibration materials associated with the actual thicknesses of the tissue samples. For example bones of known bone mineral content are placed on the subject table and attenuation images are produced. An equivalent thickness of aluminum is then derived from the image using the equations such as equation 3a, and the thickness of aluminum is associated with a given bone mineral content. Similarly, a muscle tissue sample is imaged and related to an equivalent thickness of acrylic. The calibration materials are selected so that the relationship is substantially directly proportional. In typical embodiments, step 460 is performed once in the laboratory and the results used repeatedly in subsequent calibrations efforts.

In step 470, tissue density is determined based on the equivalent thicknesses of the calibration materials. Tissue density is expressed as mass per unit area and refers to the total mass of tissue in the volume of the x-ray beam impinging on a receptor divided by the area of the receptor. Example relationships between x-ray attenuation, and tissue density are depicted in FIG. 4C, FIG. 4D and FIG. 4E.

Figure 4C:
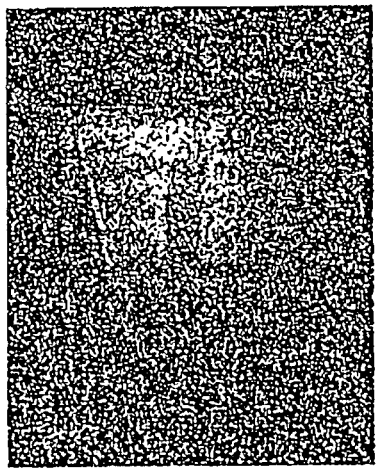
FIG. 4C is a radiograph of x-ray attenuation through a test subject at one photon energy, according to an embodiment.

FIG. 4C is a radiograph of x-ray fluence through a test subject at one photon energy, according to an embodiment. The radiograph is an image composed of a large number of pixels corresponding to individual receptors in a detector. The image is displayed such that the fluence is least at the brightest pixels. The test subject is a ham. Attenuation at the photon energy of the radiograph is computed based on the fluence represented by the radiograph image and the fluence computed based on the fluence monitor according to equation 1, above. For example, attenuation HH at each pixel is determined.

Figure 4D:
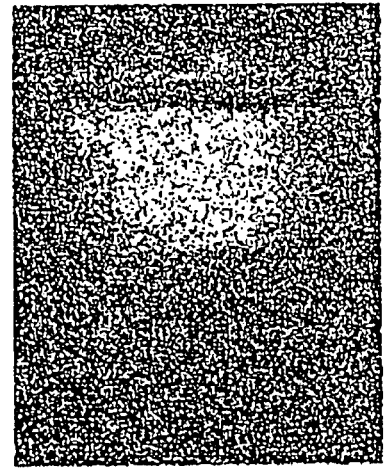
FIG. 4D is an image of muscle tissue density based in part on the radiograph of FIG. 4C according to an embodiment.
Figure 4E:
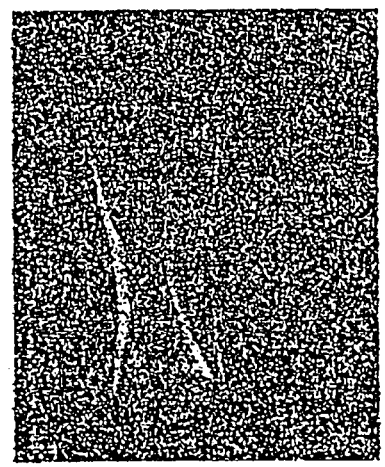
FIG. 4E is an image of bone mineral density based in part on the radiograph of FIG. 4C according to an embodiment.

FIG. 4D is an image of muscle tissue density based in part on the radiograph of FIG. 4C according to an embodiment. FIG. 4E is an image of bone mineral density based in part on the radiograph of FIG. 4C according to an embodiment. The muscle density and bone mineral density are also based on attenuation computed from a radiograph at a second photon energy, not shown. For example, HL is determined at each pixel of the second radiograph. The two attenuations HH and HL at each pixel are used with the pair of functions of attenuation, e.g., equations 3a and 3b, to compute equivalent thicknesses of the calibration materials, e.g., aluminum and acrylic. The proportionality relationship is then used to compute the tissue density based on the equivalent thicknesses of the calibration materials. For example, bone mineral density is determined based on the equivalent thickness of aluminum; and muscle density is determined based on the equivalent thickness of acrylic.

In step 480, the attenuation calibration is monitored with time by detecting the attenuation through samples of calibration material at the source. For example, as shown in FIG. 2B, the fluence monitor 137 in the source assembly 130 includes three receptors 272 for x-ray fluence. A first receptor 272a is exposed to the source directly. A second receptor 272b is blocked by a fixed thickness of a first calibration material, such as aluminum. A third receptor 272c is blocked by a fixed thickness of a second calibration material, such as acrylic. Attenuation through the first material at the source is determined by using the fluence measured in the first and second receptors as F0 and Fs in equation 1, respectively. Attenuation through the first material at the source is determined by using the fluence measured in the first and third receptors as F0 and Fs in equation 1, respectively.

A change of the attenuation at the source in either material detected in step 480 indicates a change in the photon-energy distribution of the beam or other characteristic of the beam that affects the validity of the coefficients derived for the function of attenuations, such as in equations 3a and 3b. The validity of the equivalent thicknesses and the tissue densities is also affected. An operator uses the information to determine whether the system should be repaired or recalibrated.

3.2 Dynamic Exposure

Figure 5:
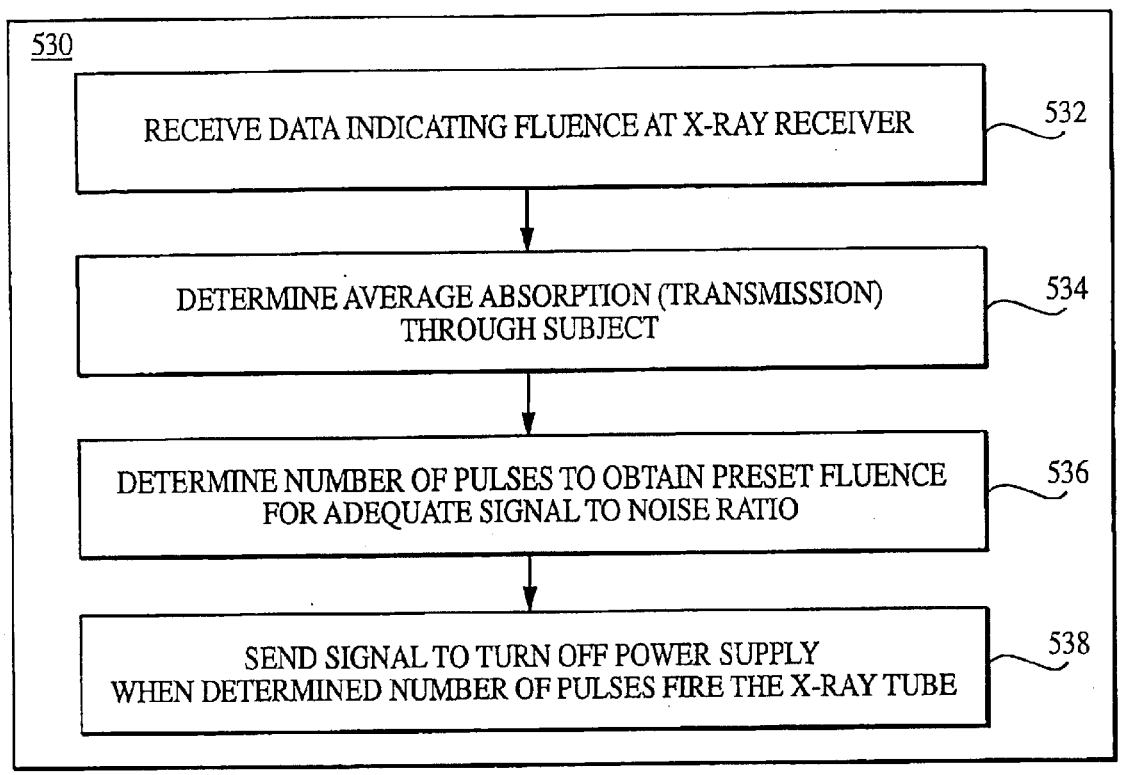
FIG. 5 is a flow cart illustrating details of a step of the flow chart of FIG. 3 for controlling exposure, according to an embodiment.

In some embodiments, an exposure control system is implemented as a process executing on computer system 160. FIG. 5 is a flow cart illustrating details of an embodiment 530 of step 330 of the flow chart of FIG. 3 for performing exposure control. In step 532, data is received by the exposure control process running on computer system 160. The data indicates fluence of x-rays at the x-ray detector up to a particular time. For example, data indicating visible photon intensity at substantially all receptors of an amorphous silicon detector array are received up to a time corresponding to 10 pulses of 1 microsecond duration from the beam source assembly. In some embodiments, only data from receptors in a central portion of the area detector 252 are received.

In step 534, the average attenuation through the subject is computed. In some embodiments this includes correcting the visible photon intensity at each pixel for geometric spreading from a spherical intensity front to the flat detector surface, for estimated scattering, and for glare using procedures well known in the art. In these embodiments, the intensity so corrected is divided by the intensity computed based on the measured fluence at the fluence monitor 137. Attenuation H is computed using equation 1. In some embodiments, the attenuation is averaged over pixels only in a central portion of the area detector.

In step 536 the exposure time is computed to achieve a target fluence and predetermined adequate SNR. For example, the number of pulses for the current photon-energy beam is computed by dividing the target fluence by a function of the average attenuation and the beam fluence computed for the detector based on the fluenc monitor 137. In some embodiments, the number of pulses for both the current photon-energy beam and the next photon-energy beam is computed. In such embodiments, step 536 can be omitted during the exposure control of the next photon-energy beam.

In step 538 a signal is sent to turn off the power supply when the number of pulses determined in step 536 have been fired. In one embodiment, the computer system 160 sends a signal to the power supply to stop when the number of pulses have been received. In another embodiment, the number of pulses is sent to a control circuit of the power supply 140, and the control circuit stops the power supply after the determined number of pulses.

3.3 Bone Properties from Multiple Angles

In some embodiments, a process executing on computer system 160 determines bone properties based on image data received from several projection angles. For example, bone position relative to positions of source and receiver assemblies can be deduced. The bone position determines the distance from bone to detector and therefore the magnification factor for bone structural features. Thus bone mineral cross sections can be produced with the correct magnification corrections. In addition, paths that do not intersect bone can be used to determine how much of the soft tissue mass is lean and how much is fat for use in pixels at other projections that include some bone mass. This allows images to be generated at each projection that accurately subtract soft tissue for pixels that include bone attenuation. Because each pair of exposures produces a two-dimensional image, bone orientation, width, cross sectional areas and moments of inertia can be computed at several points along the long axis of the bone from a single exposure.

Figure 6A:
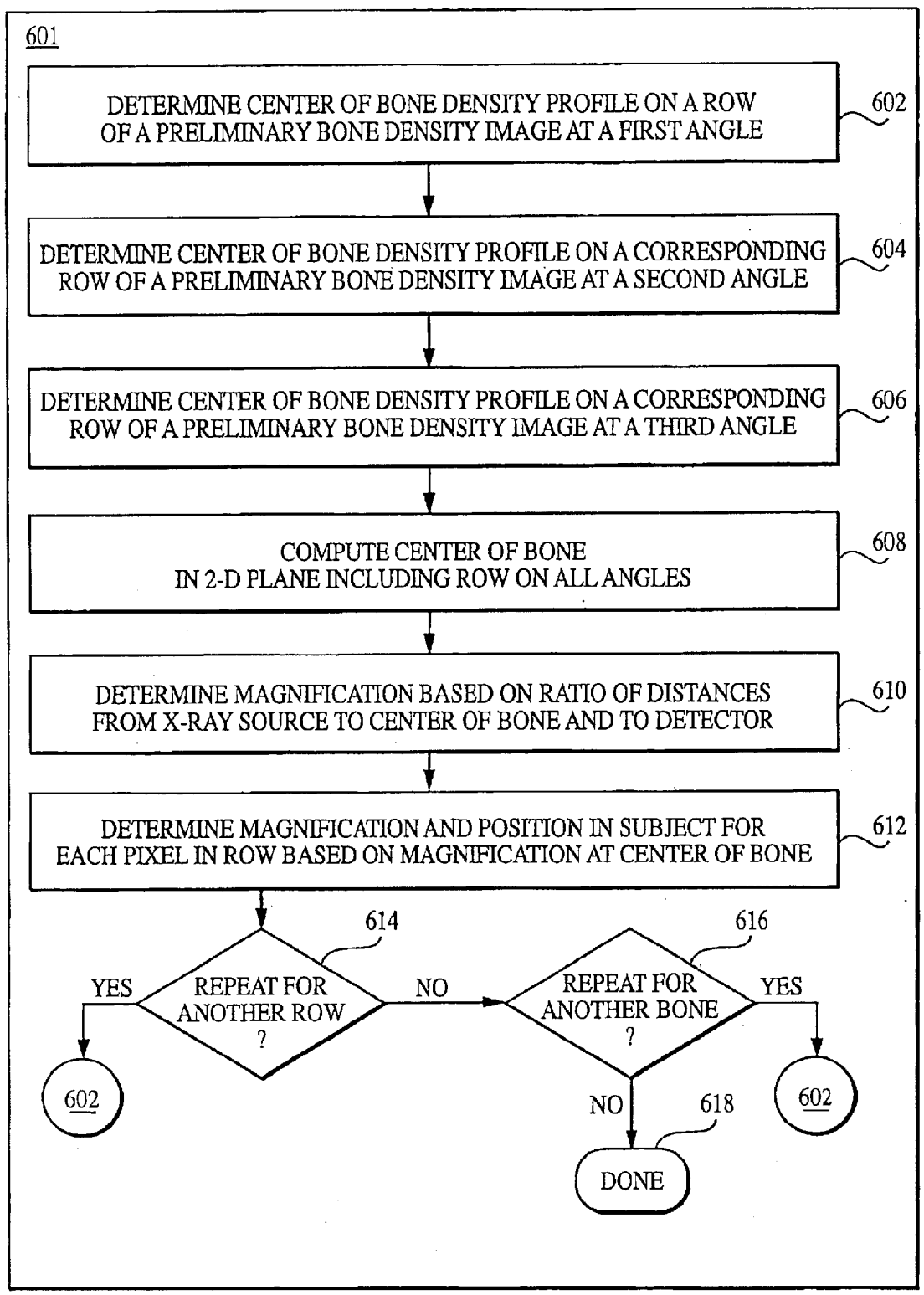
FIG. 6A is a flow cart illustrating details of a step of the flow chart of FIG. 3 for determining magnification, according to an embodiment.

FIG. 6A is a flow cart illustrating details of an embodiment 601 of step 370 of the flow chart of FIG. 3. In step 602, a center of a bone is determined along a one of one or more rows of pixels in a first image of pixels representing bone mineral density at a first projection angle. In step 604, a center of a bone is determined along a corresponding row of a second image of pixels representing bone mineral density at second projection angle is received. The focal point in the x-ray tube and the bone center pixel on a row of the detector at the first angle defines a line segment in the X-Z plane of FIG. 1B. The focal point in the x-ray tube and the bone center pixel on a row of the detector at the second angle defines a second line segment in the X-Z plane of FIG. 1B. The intersection of the two line segments indicates the position of the center of the bone in that plane. Thus, in step 608, the bone position can be determined for the plane containing that row of pixels. The bone position in other planes is determined using other rows, based on steps 614, described below.

To reduce the positional error of the bone in the X-Z plane, similar line segments are determined for other projection angles. For example, in step 606, a center of the bone is determined along the corresponding row in a third image of pixels representing bone mineral density at third projection angle. The third line segment is used in with the line segments from the other two projections to compute the bone center in step 608.

In step 610, the magnification factor is computed at each pixel based on the ratio of the distance to the detector divided by the distance to the bone center. The distance to the bone is determined by the position of the bone and the position of the focal point of the x-ray tube at a given projection angle. The distance to the detector increases for a flat detector from the pixel at the center of the beam to pixels at the outer edge of the detector, therefore the magnification factor is different for each pixel in the image. In step 612 the magnification of each pixel, and a position in the subject relative to the bone center, is computed for each pixel in the row of the images.

Step 614 represents a decision point to determine whether the magnification factor has been computed for enough rows in the image. In some embodiments, the long axis of the bone is in the X-Y plane, so that the magnification computed at one row applies to all the rows. In some embodiments, the long axis of the bone is tilted with a component int he Z direction so that magnification is different in different rows. If the bone is straight a magnification in a different row is enough to interpolate or extrapolate to the magnification in every other row. The decision point may be made in any manner know in the art. It can be implemented as a branch point in program logic or by a procedure in aligning a subject.

Step 616 represents a decision point to determine whether the magnification factors should be computed for pixels in the vicinity of another bone. If not, the process is complete as represented by the terminal step 618. If another bone is to be handled, control passes back to step 602.

Conventional DXA systems use an estimated magnification factors. Using the magnification factors determined above are more accurate than estimates, in general consequently, the area in the subject represented by each pixel can be determined more accurately. Therefroe, the bone mineral density value is more accurate than in the conventional DXA systems.

Figure 6B:
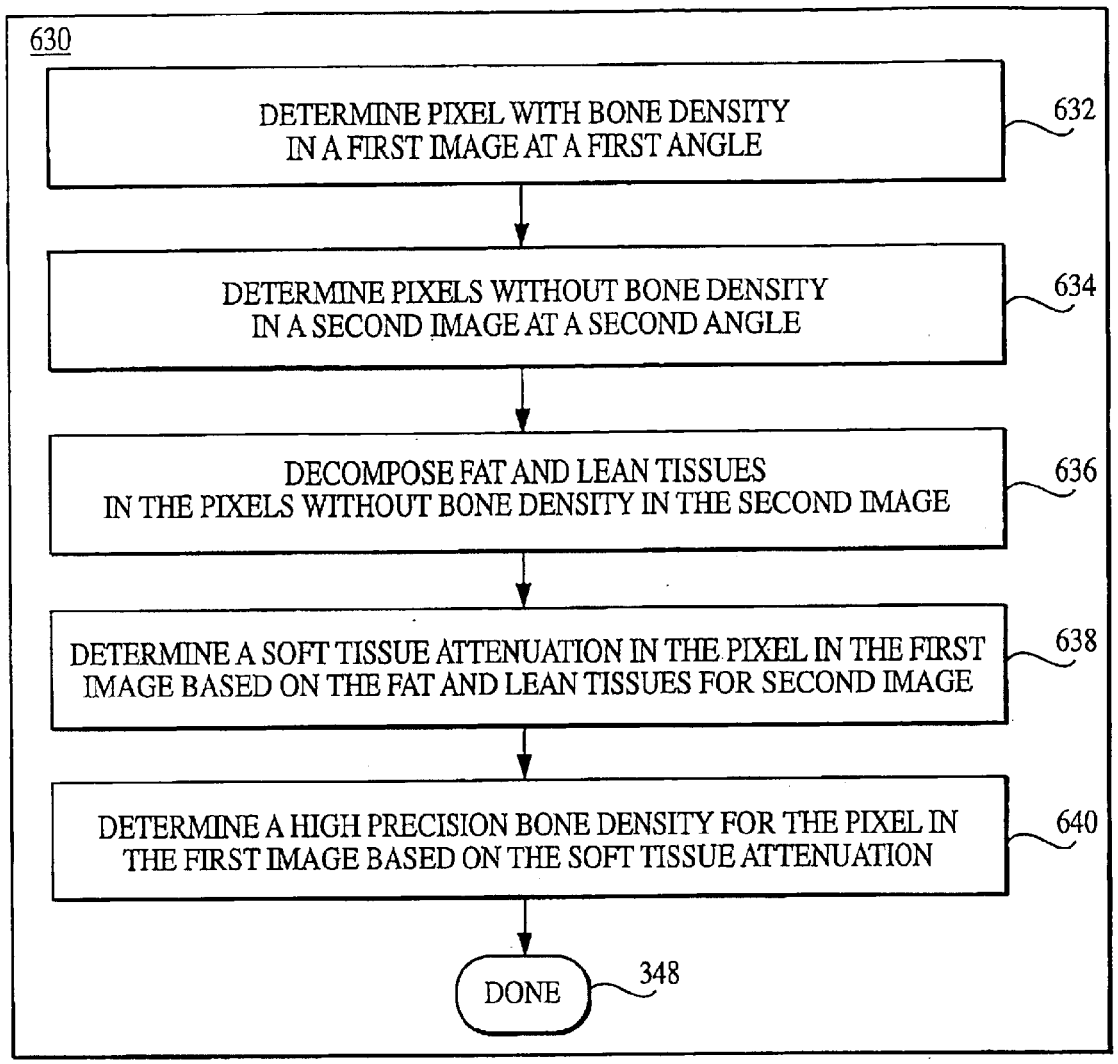
FIG. 6B is a flow cart illustrating details of a step of the flow chart of FIG. 3 for determining soft tissue decomposition for pixels measuring bone properties, according to an embodiment.

FIG. 6B is a flow cart illustrating details of an embodiment 630 of step 370 of the flow chart of FIG. 3 for determining soft tissue decomposition for pixels measuring bone properties. In a conventional DXA system the soft tissue above and below the bone, in the portion of the x-ray beam striking the receptor corresponding to the pixel, is assumed to have the same composition as the soft tissue on the sides of the bone. According to an embodiment, the composition of the soft tissue above and below the bone is determined based on images of fat tissue density and lean (muscle) tissue density at other projection angles.

In step 632, a particular pixel is selected that has a non-zero bone mineral density value (such as a bone mineral density corrected for magnification factors) based on functions of attenuation at two x-ray photon energies.

In step 634, pixels above and below the bone are determined in different photon-energy attenuation images at a second angle. In step 636, the two attenuation images at the second angle are decomposed into fat tissue and muscle (lean) tissue densities at the pixels above and below the bone.

In step 638, the soft tissue attenuation in the particular pixel is determined based on the fat tissue and lean tissue densities determined in step 636.

In step 640, the bone mineral density at the particular pixel is recomputed using the soft tissue attenuation determined in step 638. The resulting bone mineral density is more accurate, in general, than the bone mineral density assuming the soft tissue proportions in the same image to either side. Thus the bone mineral density is more accurate, in general, than is obtained from a conventional DXA system.

Figure 6C:
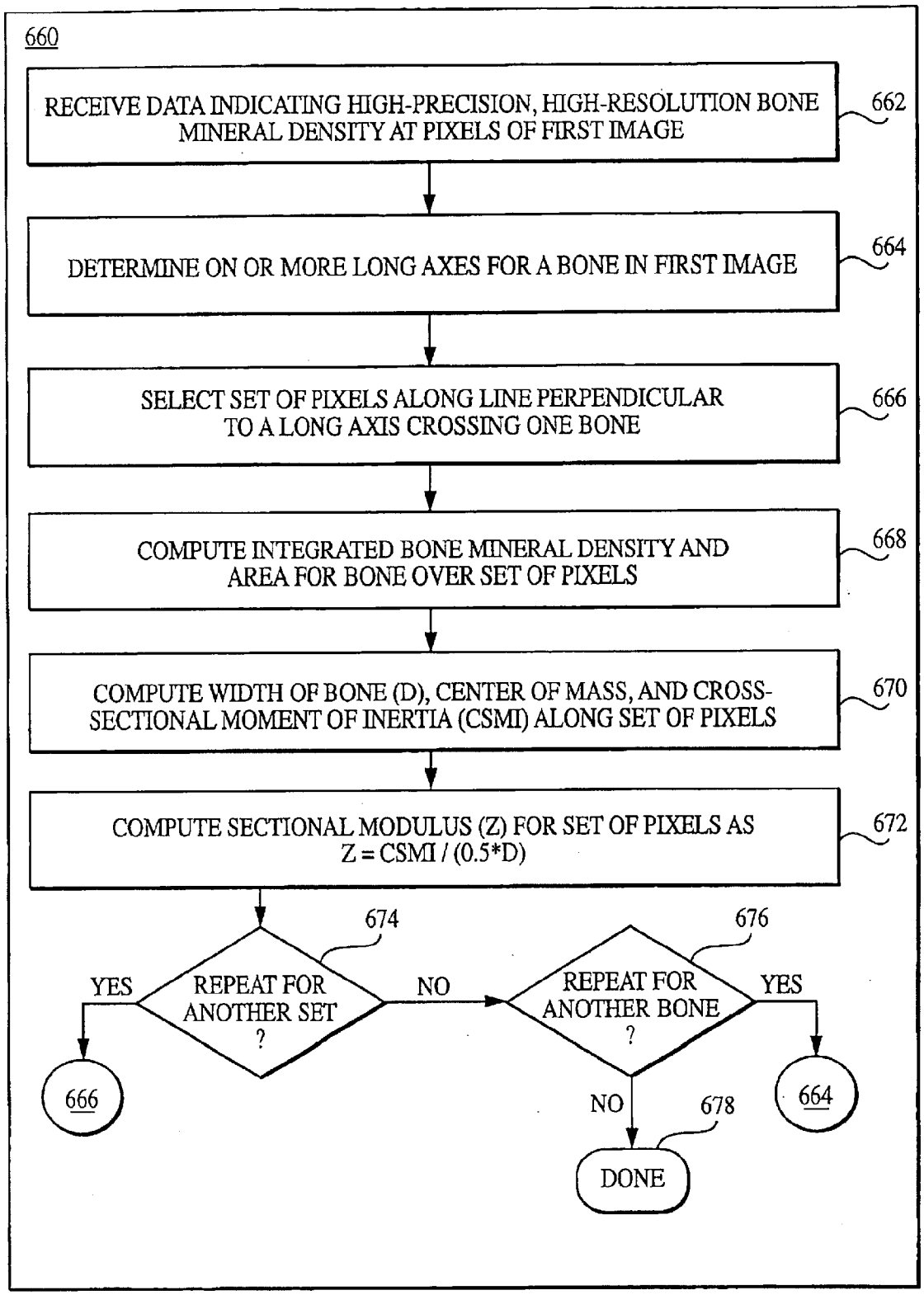
FIG. 6C is a flow cart illustrating details of a step of the flow chart of FIG. 3 for determining bone properties cross sections, according to an embodiment.

FIG. 6C is a flow cart illustrating details of an embodiment 660 of step 370 of the flow chart of FIG. 3 for determining bone properties cross sections. In some embodiments, the steps of FIG. 6C are performed on bone mineral density images using assumed magnification, or assumed soft tissue composition, or both. In a preferred embodiment, the steps of FIG. 6C are used on high-precision bone mineral density with computed magnification factors and soft tissue compositions based on multiple projections angles with high-resolution pixels of more than two pixels per millimeter in the subject.

Figure 9A:
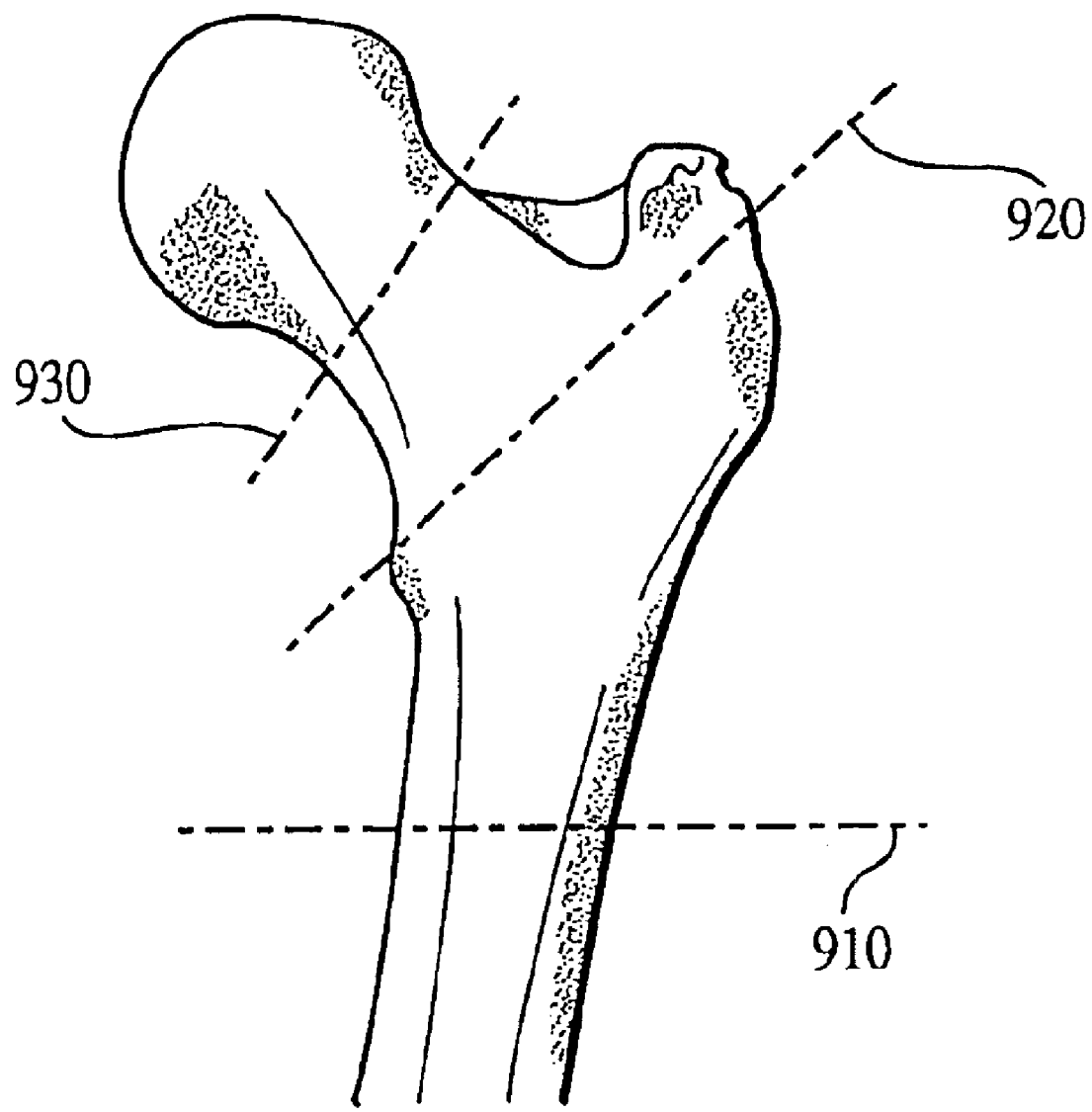
FIG. 9A is an image showing bone mineral density produced according to steps of the method in FIG. 3, according to an embodiment.

In step 662 a process executing in the computer system 160 receives data indicating bone mineral density at pixels of a first image. For example, FIG. 9A depicts a high-precision, high-resolution image of bone mineral density for a hipbone according to one embodiment.

In step 664, one or more long axes for the bone are determined. For example, the hipbone has a long axis determined for the portion of the bone below line 920 and a second long axis determined for the portion of the bone above line 920.

Figure 9B:
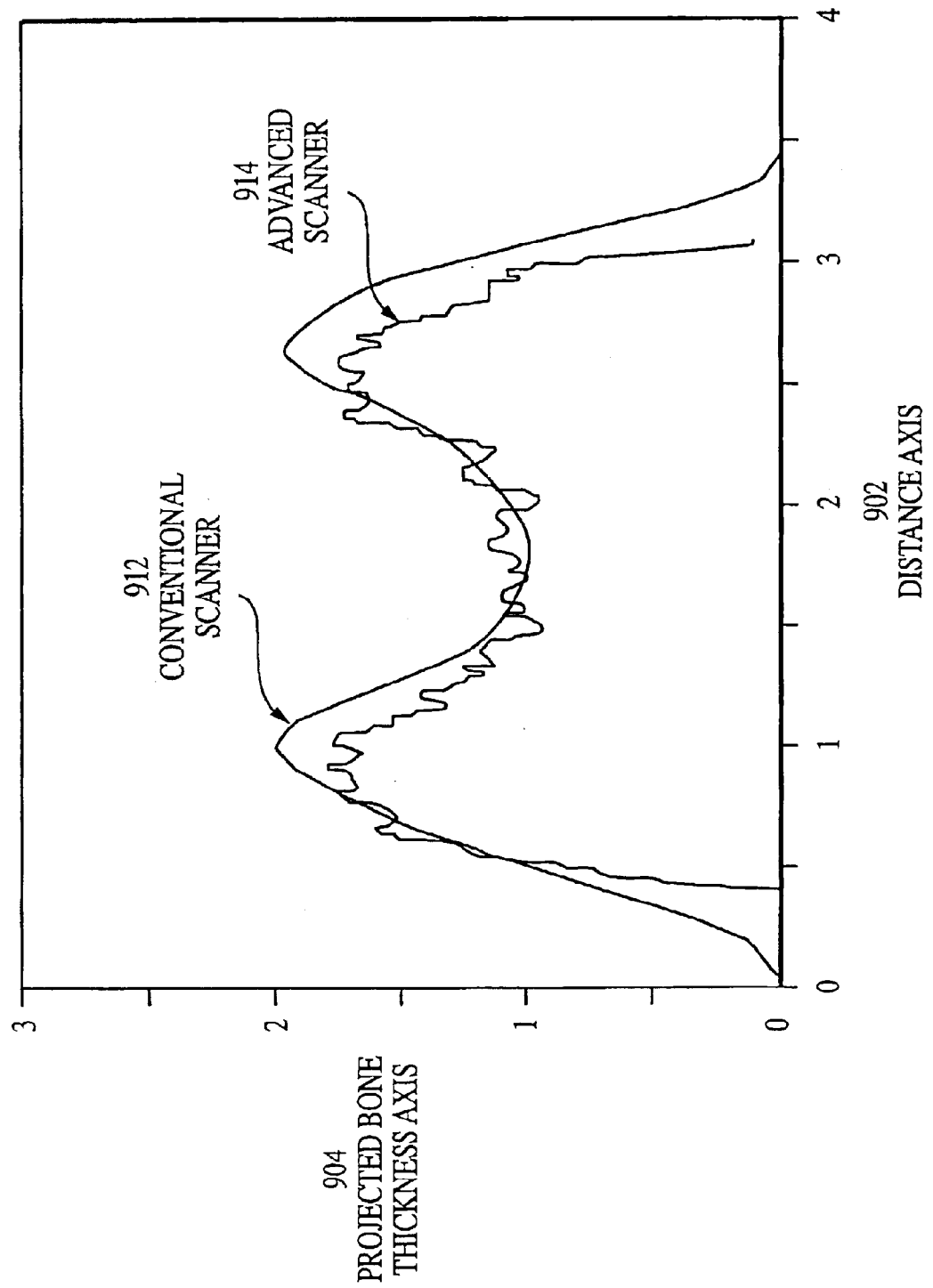
FIG. 9B is a graph showing a bone density cross section produced according to steps of the method in FIG. 6C, according to an embodiment.

In step 666, a set of pixels that crosses the bone perpendicularly to one of the long axes is selected. For example, the set of pixels indicated by line 910 or line 920 or line 930 in FIG. 9A is selected. Assume Xp is the pixel spacing (corrected for magnification) in centimeters and that BMDi is the bone mineral density (corrected for soft tissue composition) in grams per square centimeter at the ith pixel of the set of pixels. The projected bone thickness TBi at the ith pixel is given by equation 4

$$TBi=BMDi/\rho \quad (4)$$

where $\rho$ is the effective density of bone mineral in bone tissue in grams per cubic centimeter. FIG. 9B is a graph showing a bone density cross section produced according to step 666, according to one example embodiment. The bone mineral density is plotted as projected bone thickness TBi in centimeters on axis 904 against distance in the sample in centimeters on axis 902. Trace 914 represents the projected bone thickness in an example cross section, and trace 912 represents the projected bone thickness is a similar cross section from a conventional DXA scanner. The detailed features of trace 915 are reproducible and indicates both much higher spatial resolution and greater precision in the advanced scanner.

In step 668, a value for the integrated bone mineral density and for bone area is computed. The integrated bone mineral density, M, is given by equation 5.

$$M=Xp^2 * \Sigma BMDi \quad (5)$$

where the summation is over the pixels in the set. The bone cross sectional area ACS (the area of the bone) is given by equation 6.

$$ACS=(Xp*\Sigma BMDi)/\rho \quad (6)$$

In step 670, the width of the bone, D, the center of mass of the bone XCM and the cross sectional moment of inertia CSMI is computed for the first set of pixels. For example, the width of the bone D is determined by the difference in the distance (about 2.7 cm) between the two locations (1.4 cm and 3.1 cm) in FIG. 9B where the trace 914 intersects the distance axis 902 where the projected bone thickness is zero. The center of mass XCM of the bone is computed as distance weighted mass divided by the total mass, such as given in equation 7.

$$XCM=(\Sigma Xi*BMDi)/M \quad (7)$$

where Xi is the position in the subject of the ith pixel.

CSMI is computed in any manner known in the art. For example, CSMI is given by equation 8.

$$CSMI=Xp*(\Sigma(Xi-XCM)^2*BMDi)/\rho \quad (8)$$

In step 672, the sectional modulus Z is computed for the first set of pixels based on the moment of inertia. The modulus Z indicates the maximum bending stress in the plane of the image and is a measure of the strength of the bone at the cross section. The modulus Z may be computed in any manner known in the art. For example, the modulus Z is computed according to equation 9.

$$Z=2* CSMI/D \quad (9)$$

Step 674 represents a decision point to determine whether the cross sectional properties have been computed for enough rows in the image. The properties at several cross sections can be computed from the same image. If it is determined to compute cross sectional properties at another set of pixels control passes back to step 666 to select the next step. For example a set of pixels along lines 920 and 930 are selected in subsequent visits to step 666. The decision point may be made in any manner know in the art. It can be implemented as a branch point in program logic or by a procedure in aligning a subject. In one example embodiment the cross sectional properties are computed for eleven cross sections separated by 0.5 cm.

Step 676 represents a decision point to determine whether the cross sectional properties should be computed for another bone. If not, the process is complete as represented by the terminal step 678. If another bone is to be handled, control passes back to step 664.

3.4 3-D Model Formation

Figure 7:
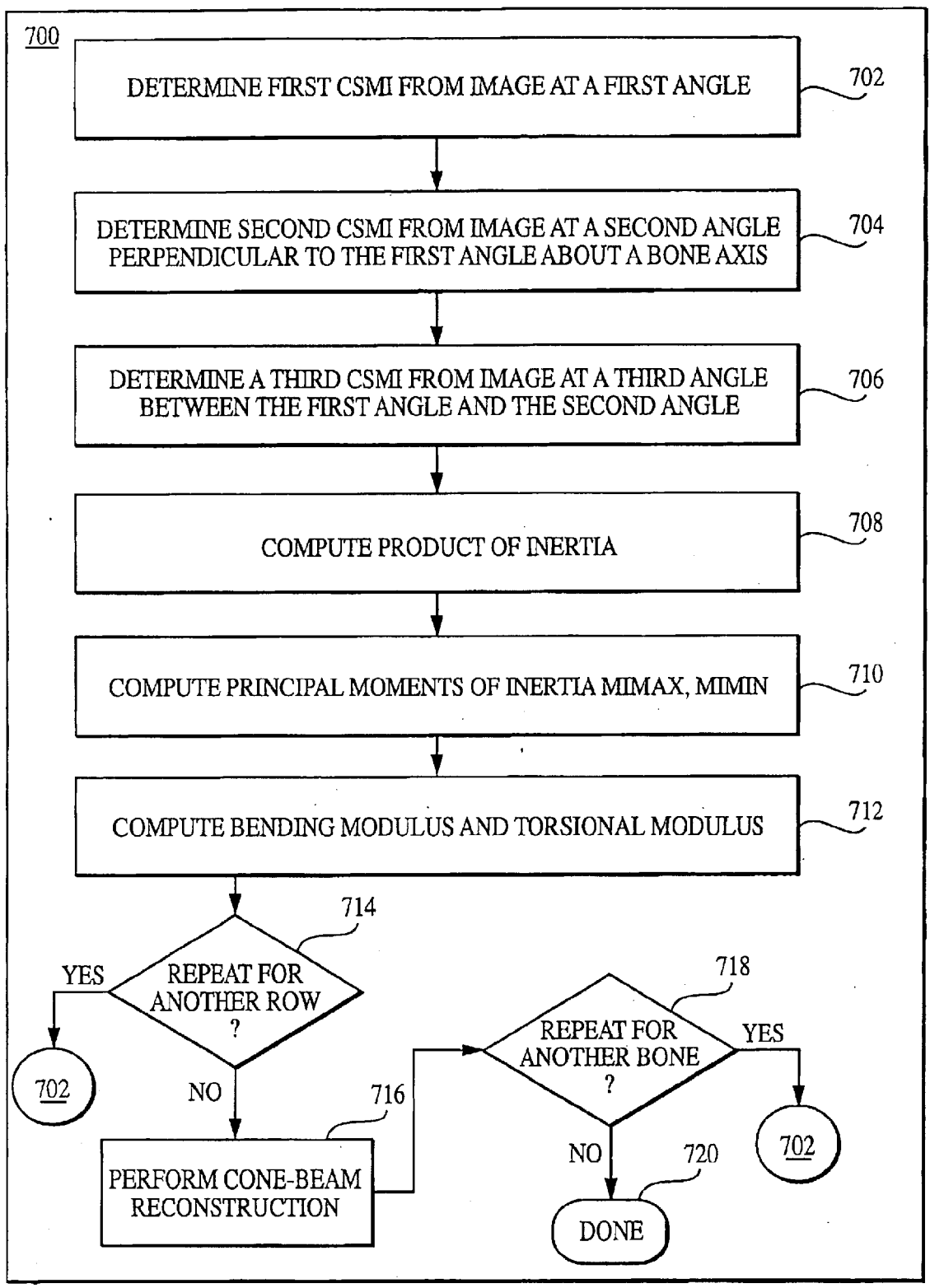
FIG. 7 is a flow cart illustrating details of a step of the flow chart of FIG. 3 for determining a 3-D model of a bone, according to an embodiment.

According to embodiments the cross sectional properties at several projection angles are combined to form a three-dimensional model of one or more bones. FIG. 7 is a flow cart illustrating details of an embodiment 700 of a step 390 of the flow chart of FIG. 3 for determining a 3-D model of a bone.

In step 702, a first cross sectional moment of inertia, CSMI1, is determined from image data from a first projection angle, such as using the method in FIG. 6C. In step 704, a second cross sectional moment of inertia, CSMI2, at a corresponding location in the same bone is determined from image data from a second projection angle, such as using the method in FIG. 6C. The second angle is in the X-Z plane with the first angle but rotated by 90 degrees. Therefore the two moments of inertia CSMI1 and CSMI2 are orthogonal and add to a constant polar moment of inertia.

In step 706, a third cross sectional moment of inertia, CSMI3, is determined from image data from a third projection angle, such as using the method in FIG. 6C. The third projection angle is between the first and second angles in step 708, according to the rotational axis principle, CSMI- is used with CSMI1 and CSMI2 to generate the product of inertia PI.

In step 710, the principal moments of inertia MImax and MImin are computed in any manner known in the art. For example MImax and MImin are computed from CSMI1, CSMI2 and PI according to equations 10a and 10b.

$$MImax=(CSMI1+CSMI2)/2+\sqrt{\{[(CSMI1-CSMI2)/2]^2+PI^2\}} \quad (10a)$$

$$MImin=(CSMI1+CSMI2)/2-\sqrt{\{[(CSMI1-CSMI2)/2]^2+PI^2\}} \quad (10b)$$

Figure 9C:
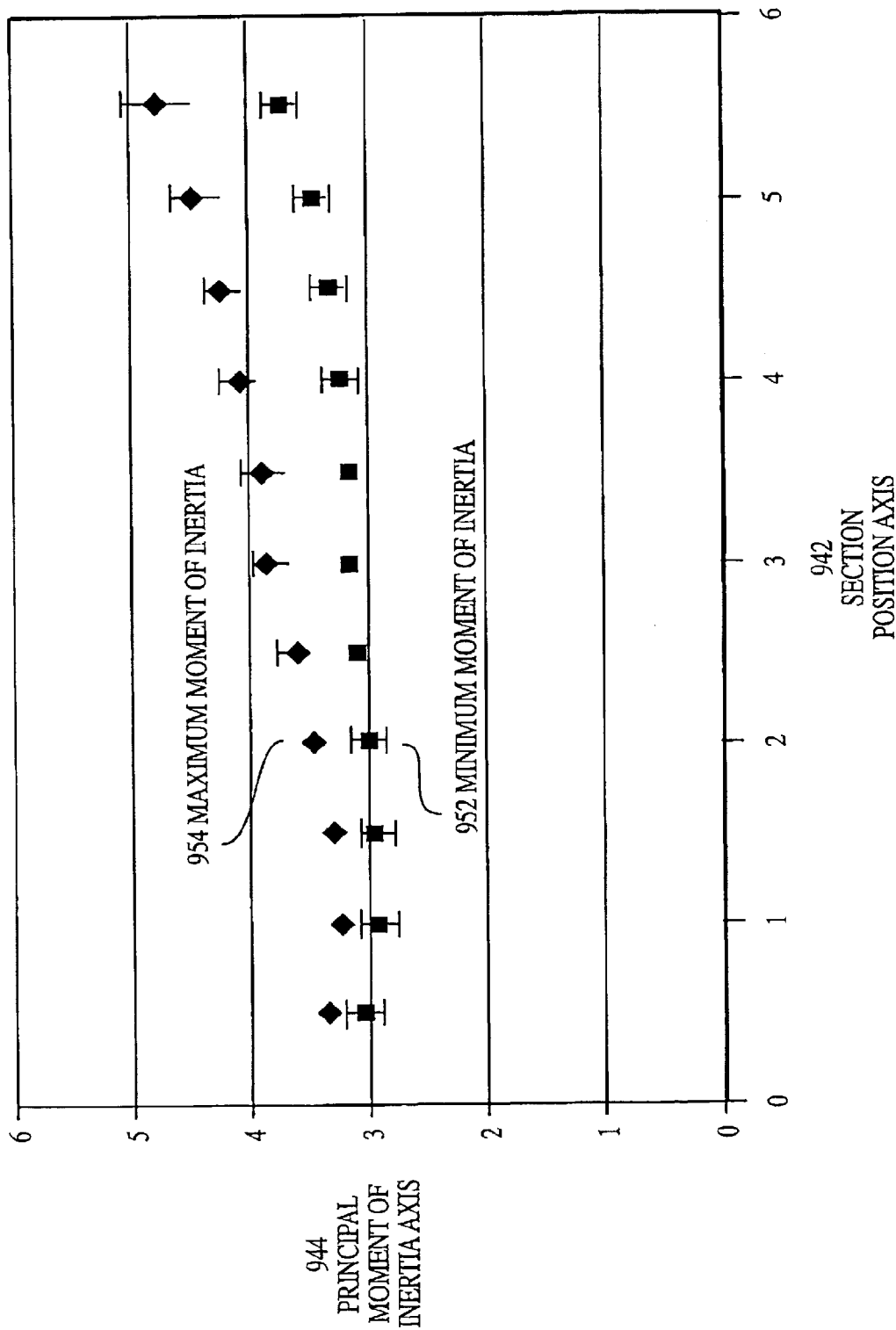
FIG. 9C is a graph showing principal moments of inertia of a bone produced according to steps of the method in FIG. 7, according to an embodiment.

FIG. 9C is a graph showing principal moments of inertia of a bone produced according to steps of the method in FIG. 7, according to the example embodiment. Errors are about two to three percent. It is expected that using the high-precision, high-resolution bone mineral density images, the principal moments of inertia may be computed with errors less than about one percent.

In step 712 a bending modulus and a torsional modulus are computed from the principal moments of inertia that define the bone strength against loading stresses in any configuration.

Step 714 represents a decision point to determine whether the principal moments of inertia have been computed for enough locations on the bone. The principal moments at several cross sections can be computed from the same set of images at the three or more projection angles. If it is determined to compute principal moments of inertia at another location on the bone, control passes back to step 702 to select the next cross section. The decision point may be made in any manner know in the art. It can be implemented as a branch point in program logic or by a procedure in aligning a subject. The use of three projections may not be adequate in cases where there are two bones, such as the lower leg, because the two bones overlap in some projections. It is anticipated that five projections are adequate in those cases. In some embodiments, therefore, the data used in steps 702, 704, 706 are taken from images selected from five or more projection angles. A different set of three images may be selected for different locations along the long axis of a bone. In one example embodiment the principal moments of inertia computed for eleven cross sections separated by 0.5 cm using images from five or more projection angles.

Figure 9D:
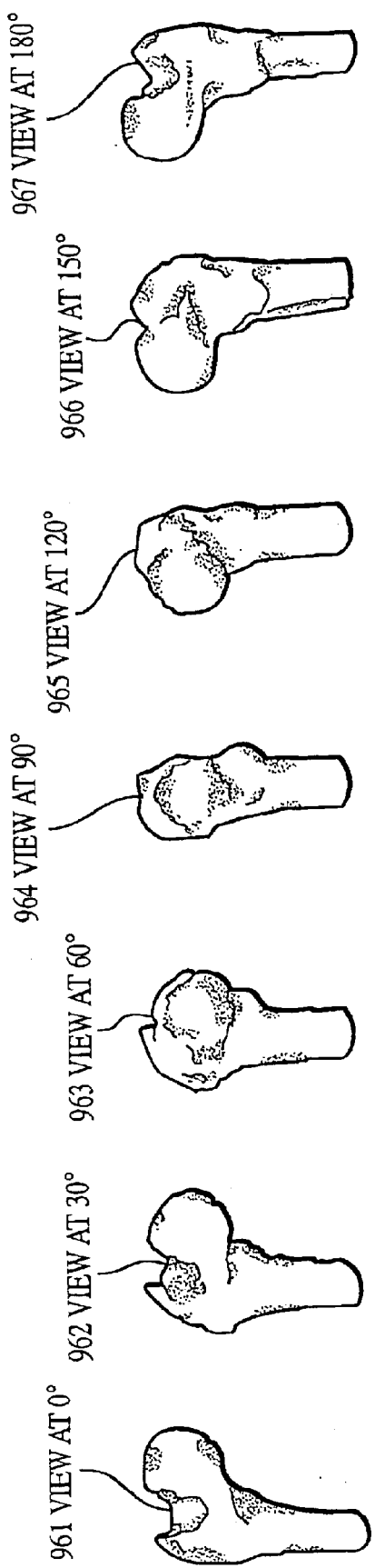
FIG. 9D is a sequence of images depicting a cone-beam reconstruction used to construct a 3-D model according to steps of the method in FIG. 7.

When no further principal moments of inertia and strength moduli are to be computed, control passes to step 716. In step 716 cone-beam reconstruction is employed to complete a three-dimensional model of the bone. It is anticipated that a cone-beam reconstruction with from three to seven projections is adequate to produce a pseudo 3-D geometry that is mechanically equivalent to a measured hip. FIG. 9D is a sequence of seven images depicting a cone-beam reconstruction used to construct a 3-D model according to steps of the method in FIG. 7.

Step 718 represents a decision point to determine whether the cross sectional properties should be computed for another bone. If not, the process is complete as represented by the terminal step 678. If another bone is to be handled, control passes back to step 702.

3.5 Risk of Injury

Figure 8:
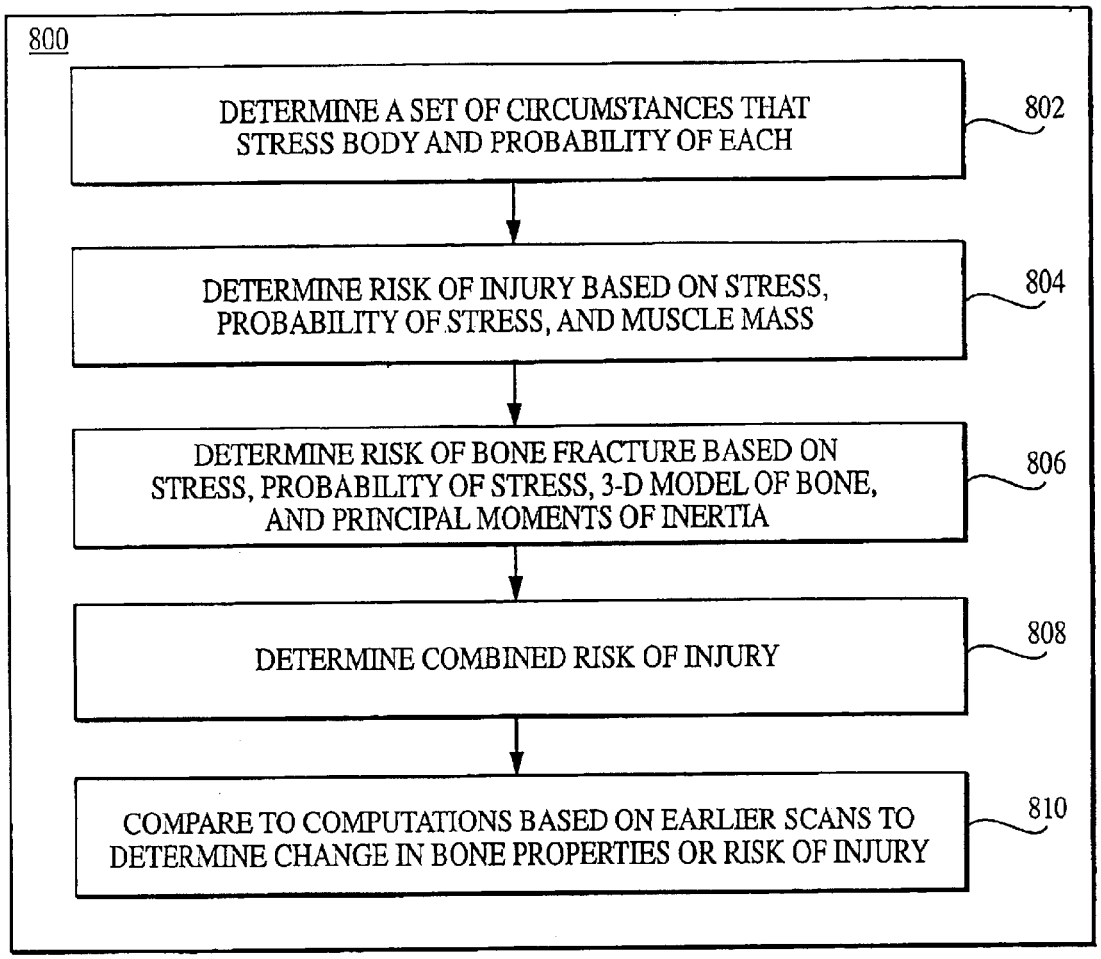
FIG. 8 is a flow cart illustrating details of a step of the flow chart of FIG. 3 for computing risk of injury, according to an embodiment.

FIG. 8 is a flow cart illustrating details of a step of the flow chart of FIG. 3 for computing risk of injury, according to an embodiment.

In step 810, the images and bone properties, included risk of injury, are compared to images taken at a previous time—days, months, or years earlier. Any significant differences would indicate changes in properties and risk. Efficacy of countermeasures may be quantified in terms of rate of change of risk of injury based on such comparisons.

Such comparisons are especially useful for the hipbone. Any three dimensional reconstruction of the hipbone in a normal human would not exclude the pelvis bone which inhibits the computation of cross sectional properties and principal moments of inertia. It is possible to determine whether there has been a significant change of strength from a previous measurement by comparing images for a particular image plane. The particular image plane is chosen so that it can be imaged in all subjects. Any structural changes noted by comparing images in that plane from different times would indicate bone changes due to loading, disease, countermeasures, or any combination of such factors.

Furthermore, individuals can be compared by comparing images in the particular plane. The ideal particular plane for the hipbone is the plane containing the angle between the hipbone shaft and the hipbone neck. An image in the ideal plane of a patient can be compared to an image of the same plane for a second patient or normal subject. Differences would indicate abnormalities or difference in bone strength, even if principal moments of inertia cannot be derived. The gantry of embodiments of the present invention allows the source and receiver to be rotated so that the x-ray beam is perpendicular to the ideal plane.

4. Computer Hardware Overview

Figure 10:
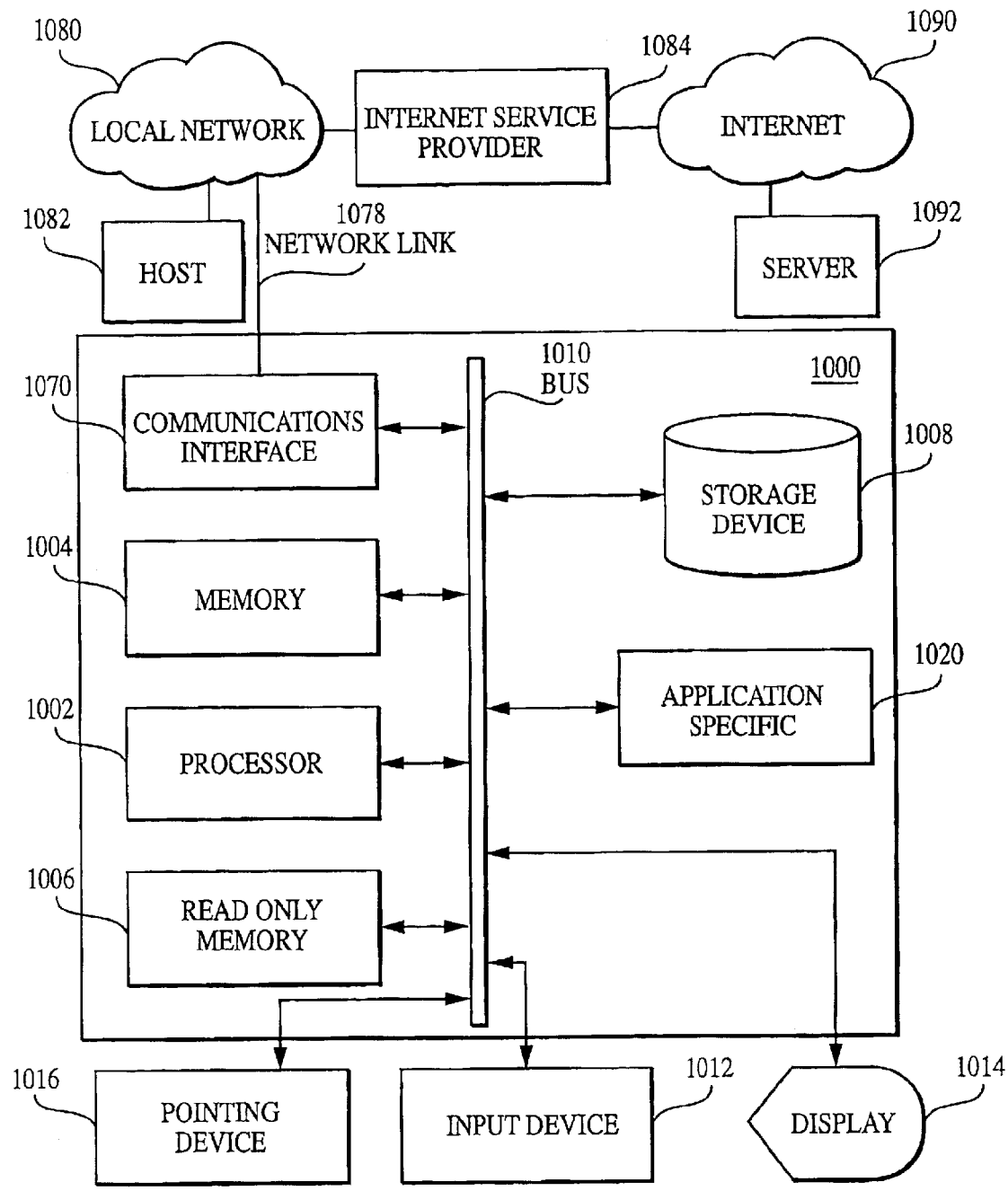
FIG. 10 is a block diagram that illustrates a computer system upon which embodiments may be implemented.

FIG. 10 is a block diagram that illustrates a computer system 1000 upon which an embodiment of some processes of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular and atomic interactions. For example, north and south magnetic fields, or a zero and non-zero electric voltage, represent two states (0, 1) of a binary digit (bit). A sequence of binary digits constitute digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information. The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitute computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor. 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. For wireless links, the communications interface 1070 sends and receives electrical, acoustic or electromagnetic signals, including infrared and optical signals, that carry information streams, such as digital data. Such signals are examples of carrier waves.

The term computer-readable medium is used herein to refer to any medium that participates in providing instructions to processor 1002 for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. Signals that are transmitted over transmission media are herein called carrier waves.

Common forms of computer-readable media include, for example, a floppy disk, a flexible disk, a hard disk, a magnetic tape, or any other magnetic medium, a compact disk ROM (CD-ROM), or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, which carry information to and from computer system 1000, are exemplary forms of carrier waves. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to an infra-red signal, a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method for deriving bone properties from dual-energy x-ray absorptiometry images, the method comprising:
   receiving first image data comprising pixels indicating attenuation through a plurality of known thicknesses of a first two calibration materials at a first photon energy;
   receiving second image data comprising pixels indicating attenuation through the plurality of known thicknesses of the first two calibration materials at a second photon energy;
   determining first conic surface function relating attenuation data from first image data to the plurality of known thicknesses;
   determining second conic surface function relating attenuation data from second image data to the plurality of known thicknesses;
   inverting the first conic surface function and the second conic surface function to determine a pair of thickness functions, each thickness function relating thickness of one calibration material to attenuations from the first image data and the second image data; and
   applying the pair of thickness functions with attenuations from image data comprising pixels indicating attenuation through tissue of a subject.

2. The method of claim 1, wherein the first two calibration materials correspond to fat tissue and lean tissue.

3. The method of claim 1, wherein the first image data and the second image data comprise pixels indicating attenuations with precision errors less than about one percent.

4. The method of claim 1, wherein the first image data and the second image data comprise pixels spaced closer than about two pixels per millimeter.

5. The method of claim 1, further comprising:
   receiving third image data comprising pixels indicating attenuation through a plurality of known thicknesses of a second two calibration materials at a first photon energy;
   receiving fourth image data comprising pixels indicating attenuation through the plurality of known thicknesses of the second two calibration materials at a second photon energy;
   determining third conic surface function relating attenuation data from third image data to the plurality of known thicknesses of the second two calibration materials;
   determining fourth conic surface function relating attenuation data from fourth image data to the plurality of known thicknesses of the second two calibration materials; and
   inverting the third conic surface function and the fourth conic surface function to determine a second pair of thickness functions, each thickness function of the second pair relating thickness of one calibration material of the second two calibration materials to attenuations from the third image data and the fourth image data,
   wherein said step of applying the pair of thickness functions comprises applying the second pair of thickness functions.

6. The method of claim 5, wherein:
   the first two calibration materials correspond to fat tissue and lean tissue; and
   the second two calibration materials correspond to bone tissue and soft tissue.

7. A method for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, the method comprising:
   receiving first image data comprising pixels indicating bone mineral density projected at a first angle of the plurality of projection angles;
   receiving second image data comprising pixels indicating bone mineral density projected at a different second angle of the plurality of projection angles; and
   based on the first image data and the second image data, computing a magnification factor relating distances associated with pixels in the first image data and the second image data to corresponding distances at a bone in the subject.

8. The method of claim 7, said step of computing the magnification factor further comprising:
   determining a first position at a center of a contiguous set of pixels having measurable bone mineral density along a row of the pixels in the first image data;
   determining a second position at a center of a contiguous set of pixels having measurable bone mineral density along a correspond row of the pixels in the second image data; and
   computing the magnification factor based on the first position and the second position.

9. The method of claim 7, wherein the magnification factor is different in different rows of pixels in the first image and the second image.

10. The method of claim 7, said step of computing the magnification factor further comprising computing the magnification factor for each pixel in a row of pixels in the first image data and the second image data based on a pixel position within the row of pixels.

11. The method of claim 7, said step of computing the magnification factor further comprising computing a position between the source and the receiver for a bone in the subject.

12. The method of claim 11, wherein the position for a bone in the subject is a three-dimensional position.

13. The method of claim 7, wherein the first image data and the second image data comprise pixels spaced closer than about two pixels per millimeter.

14. A method for deriving bone properties from images generated by a dual-energy x-ray absorptiometry apparatus having an x-ray source in fixed relation to an x-ray receiver, both the source and the receiver moveably mounted to measure attenuation through a subject at a plurality of projection angles, the method comprising:
   receiving first image data comprising pixels indicating attenuation of a first photon energy projected at a first angle of the plurality of projection angles;
   receiving second image data comprising pixels indicating attenuation of a second photon energy projected at the first angle;
   receiving third image data comprising pixels indicating attenuation of the first photon energy projected at a different second angle of the plurality of projection angles;
   receiving fourth image data comprising pixels indicating attenuation of the second photon energy projected at the second angle; and
   based on the first image data, the second image data, the third image data and the fourth image data, computing a value indicating a bone mineral density for a particular pixel in the first image data.

15. The method of claim 14, said step of computing the value indicating the bone mineral density further comprising:
   determining a soft tissue composition for the particular pixel based on a set of pixels without measurable bone mineral density at the second angle; and
   determining the value of the bone mineral density based on the attenuation at the particular pixel in the first image data, the attenuation at a corresponding pixel in the second image data, and the soft tissue composition for the particular pixel.

16. The method of claim 14, wherein the soft tissue composition comprises a first value for fat tissue and a second value for muscle tissue.

17. The method of claim 14, wherein the first image data, the second image data, the third image data and the fourth image data comprise pixels indicating attenuations with precision errors less than about one percent.

18. The method of claim 14, wherein the first image data, the second image data, the third image data and the fourth image data comprise pixels spaced closer than about two pixels per millimeter.

19. A method for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, the method comprising:
   receiving image data comprising pixels indicating bone mineral density projected at a first angle of the plurality of projection angles;
   determining a long axis for a bone in the image data;
   selecting a first set of pixels in the image data substantially along a line segment crossing the bone and perpendicular to the long axis; and
   based on the first set of pixels, computing cross sectional moment of inertia.

20. The method of claim 19, said step of computing the cross sectional moment of inertia further comprising:
   determining a width for the bone;
   determining a center of mass for the bone; and
   computing the cross sectional moment of inertia based on a subset within the width for the bone of the first set of pixels and the center of mass.

21. The method of claim 19, further comprising determining a sectional modulus for the bone based on the cross sectional moment of inertia.

22. The method of claim 19, further comprising determining a cross sectional area.

23. The method of claim 19, wherein the first image data comprise pixels indicating bone mineral density with precision errors less than about one percent.

24. The method of claim 19, wherein the first image data comprise pixels spaced closer than about two pixels per millimeter.

25. The method of claim 19, further comprising:
   selecting a second set of pixels in the image data different from the first set of pixels, the second set of pixels substantially along a line segment crossing the bone and perpendicular to the long axis; and
   based on the second set of pixels, computing a second cross sectional moment of inertia.

26. The method of claim 19, wherein said step of determining the long axis for the bone comprises selecting a plurality of long axis segments for the bone.

27. The method of claim 26, wherein the bone is a hip bone.

28. A method for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, the method comprising:
   receiving first image data comprising pixels indicating bone mineral density projected at a first angle of the plurality of projection angles;
   receiving second image data comprising pixels indicating bone mineral density projected at a different second angle of the plurality of projection angles;
   receiving third image data comprising pixels indicating bone mineral density projected at a third angle of the plurality of projection angles, the third angle different from the first angle and the second angle; and
   based on the first image data, the second image data and the third image data, computing principal moments of inertia for a bone in the subject.

29. The method of claim 28, wherein:
   the first angle differs from the second angle by substantially 90 degrees; and
   the third angle is between the first angle and the second angle.

30. The method of claim 28, said step of computing the principal moments of inertia further comprising:
   computing a first cross sectional moment of inertia based on the first image data;
   computing a second cross sectional moment of inertia based on the second image data;
   computing a product of inertia based on the third image data; and
   computing the principal moments of inertia based on the first cross sectional area, the second cross sectional area, and the product of inertia.

31. The method of claim 28, wherein the first image data and the second image data comprise pixels indicating bone mineral density with precision errors less than about one percent.

32. The method of claim 28, wherein the first image data and the second image data comprise pixels spaced closer than about two pixels per millimeter.

33. The method of claim 28, wherein said step of computing principal moments of inertia further comprises computing a plurality of principal moments of inertia for the bone.

34. The method of claim 28, further comprising the step of performing cone-beam reconstruction of the bone.

35. The method of claim 28, wherein:
   the method further comprises the steps of
      determining a number of additional different angles of the plurality of projection angles for resolving principal moments of inertia at a particular position along a long axis of the bone, and
      receiving additional different image data, each comprising pixels indicating bone mineral density projected at a corresponding one of the additional different angles; and
   said step of computing the principal moments of inertia for the bone comprises computing the principal moments of inertia further based on the additional different image data.

36. A method for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, the method comprising:

receiving first data indicating a plurality of principal moments of inertia for a bone in the subject based on a plurality of images taken at the plurality of projection angles;

determining a stress on the bone associated with a particular scenario;

determining a probability of the particular scenario;

determining a risk of injury based on the probability of the particular scenario, the stress associated with the particular scenario, and the plurality of moments of inertia; and reporting the risk of injury for presentation to a human operator.

37. The method of claim 36, wherein the first data indicates the plurality of principal moments of inertia with precision errors less than about one percent.

38. The method of claim 36, wherein each image of the plurality of images comprises pixels spaced closer than about two pixels per millimeter.

39. The method of claim 36, said step of computing the risk of injury further comprising:

computing a strength modulus in a plane of the stress based on the plurality of principal moments of inertia; and determining a breakage of the bone based on the stress and the strength modulus.

40. A computer-readable medium carrying one or more sequences of instructions for deriving bone properties from dual-energy x-ray absorptiometry images, wherein execution of the one or more sequences of instructions by one or more processors causes the one or more processors to perform the steps of:

receiving first image data comprising pixels indicating attenuation through a plurality of known thicknesses of a first two calibration materials at a first photon energy;

receiving second image data comprising pixels indicating attenuation through the plurality of known thicknesses of the first two calibration materials at a second photon energy;

determining first conic surface function relating attenuation data from first image data to the plurality of known thicknesses;

determining second conic surface function relating attenuation data from second image data to the plurality of known thicknesses;

inverting the first conic surface function and the second conic surface function to determine a pair of thickness functions, each thickness function relating thickness of one calibration material to attenuations from the first image data and the second image data; and applying the pair of thickness functions with attenuations from image data comprising pixels indicating attenuation through tissue of a subject.

41. The computer-readable medium of claim 40, wherein the first two calibration materials correspond to fat tissue and lean tissue.

42. The computer-readable medium of claim 40, wherein the first image data and the second image data comprise pixels indicating attenuations with precision errors less than about one percent.

43. The computer-readable medium of claim 40, wherein the first image data and the second image data comprise pixels spaced closer than about two pixels per millimeter.

44. The computer-readable medium of claim 40, wherein execution of the one or more sequences of instructions further causes the one or more processors to perform the steps of:

receiving third image data comprising pixels indicating attenuation through a plurality of known thicknesses of a second two calibration materials at a first photon energy;

receiving fourth image data comprising pixels indicating attenuation through the plurality of known thicknesses of the second two calibration materials at a second photon energy;

determining third conic surface function relating attenuation data from third image data to the plurality of known thicknesses of the second two calibration materials;

determining fourth conic surface function relating attenuation data from fourth image data to the plurality of known thicknesses of the second two calibration materials; and inverting the third conic surface function and the fourth conic surface function to determine a second pair of thickness functions, each thickness function of the second pair relating thickness of one calibration material of the second two calibration materials to attenuations from the third image data and the fourth image data, wherein said step of applying the pair of thickness functions comprises applying the second pair of thickness functions.

45. The computer-readable medium of claim 44, wherein:

the first two calibration materials correspond to fat tissue and lean tissue; and the second two calibration materials correspond to bone tissue and soft tissue.

46. A computer-readable medium carrying one or more sequences of instructions for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, wherein execution of the one or more sequences of instructions by one or more processors causes the one or more processors to perform the steps of:

receiving first image data comprising pixels indicating bone mineral density projected at a first angle of the plurality of projection angles;

receiving second image data comprising pixels indicating bone mineral density projected at a different second angle of the plurality of projection angles; and based on the first image data and the second image data, computing a magnification factor relating distances associated with pixels in the first image data and the second image data to corresponding distances at a bone in the subject.

47. The computer-readable medium of claim 46, said step of computing the magnification factor further comprising:

determining a first position at a center of a contiguous set of pixels having measurable bone mineral density along a row of the pixels in the first image data;

determining a second position at a center of a contiguous set of pixels having measurable bone mineral density along a correspond row of the pixels in the second image data; and computing the magnification factor based on the first position and the second position.

48. The computer-readable medium of claim 46, wherein the magnification factor is different in different rows of pixels in the first image and the second image.

49. The computer-readable medium of claim 46, said step of computing the magnification factor further comprising computing the magnification factor for each pixel in a row of pixels in the first image data and the second image data based on a pixel position within the row of pixels.

50. The computer-readable medium of claim 46, said step of computing the magnification factor further comprising computing a position between the source and the receiver for a bone in the subject.

51. The computer-readable medium of claim 50, wherein the position for a bone in the subject is a three-dimensional position.

52. The computer-readable medium of claim 46, wherein the first image data and the second image data comprise pixels spaced closer than about two pixels per millimeter.

53. A computer-readable medium carrying one or more sequences of instructions for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, wherein execution of the one or more sequences of instructions by one or more processors causes the one or more processors to perform the steps of:
   receiving first image data comprising pixels indicating attenuation of a first photon energy projected at a first angle of the plurality of projection angles;
   receiving second image data comprising pixels indicating attenuation of a second photon energy projected at the first angle;
   receiving third image data comprising pixels indicating attenuation of the first photon energy projected at a different second angle of the plurality of projection angles;
   receiving fourth image data comprising pixels indicating attenuation of the second photon energy projected at the second angle; and
   based on the first image data, the second image data, the third image data and the fourth image data, computing a value indicating a bone mineral density for a particular pixel in the first image data.

54. The computer-readable medium of claim 53, said step of computing the value indicating the bone mineral density further comprising:
   determining a soft tissue composition for the particular pixel based on a set of pixels without measurable bone mineral density at the second angle; and
   determining the value of the bone mineral density based on the attenuation at the particular pixel in the first image data, the attenuation at a corresponding pixel in the second image data, and the soft tissue composition for the particular pixel.

55. The computer-readable medium of claim 53, wherein the soft tissue composition comprises a first value for fat tissue and a second value for muscle tissue.

56. The computer-readable medium of claim 53, wherein the first image data, the second image data, the third image data and the fourth image data comprise pixels indicating attenuations with precision errors less than about one percent.

57. The computer-readable medium of claim 53, wherein the first image data, the second image data, the third image data and the fourth image data comprise pixels spaced closer than about two pixels per millimeter.

58. A computer-readable medium carrying one or more sequences of instructions for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, wherein execution of the one or more sequences of instructions by one or more processors causes the one or more processors to perform the steps of:
   receiving image data comprising pixels indicating bone mineral density projected at a first angle of the plurality of projection angles;
   determining a long axis for a bone in the image data;
   selecting a first set of pixels in the image data substantially along a line segment crossing the bone and perpendicular to the long axis; and
   based on the first set of pixels, computing cross sectional moment of inertia.

59. The computer-readable medium of claim 58, said step of computing the cross sectional moment of inertia further comprising:
   determining a width for the bone;
   determining a center of mass for the bone; and
   computing the cross sectional moment of inertia based on a subset within the width for the bone of the first set of pixels and the center of mass.

60. The computer-readable medium of claim 58, wherein execution of the one or more sequences of instructions further causes the one or more processors to perform the step of determining a sectional modulus for the bone based on the cross sectional moment of inertia.

61. The computer-readable medium of claim 58, wherein execution of the one or more sequences of instructions further causes the one or more processors to perform the step of determining a cross sectional area.

62. The computer-readable medium of claim 58, wherein the first image data comprise pixels indicating bone mineral density with precision errors less than about one percent.

63. The computer-readable medium of claim 58, wherein the first image data comprise pixels spaced closer than about two pixels per millimeter.

64. The computer-readable medium of claim 58, wherein execution of the one or more sequences of instructions further causes the one or more processors to perform the steps of:
   selecting a second set of pixels in the image data different from the first set of pixels, the second set of pixels substantially along a line segment crossing the bone and perpendicular to the long axis; and
   based on the second set of pixels, computing a second cross sectional moment of inertia.

65. The computer-readable medium of claim 58, wherein said step of determining the long axis for the bone comprises selecting a plurality of long axis segments for the bone.

66. The computer-readable medium of claim 65, wherein the bone is a hip bone.

67. A computer-readable medium carrying one or more sequences of instructions for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, wherein execution of the one or more sequences of instructions by one or more processors causes the one or more processors to perform the steps of:
   receiving first image data comprising pixels indicating bone mineral density projected at a first angle of the plurality of projection angles;

receiving second image data comprising pixels indicating bone mineral density projected at a different second angle of the plurality of projection angles;

receiving third image data comprising pixels indicating bone mineral density projected at a third angle of the plurality of projection angles, the third angle different from the first angle and the second angle; and based on the first image data, the second image data and the third image data, computing principal moments of inertia for a bone in the subject.

68. The computer-readable medium of claim 67, wherein:

the first angle differs from the second angle by substantially 129 degrees; and the third angle is between the first angle and the second angle.

69. The computer-readable medium of claim 67, said step of computing the principal moments of inertia further comprising:

computing a first cross sectional moment of inertia based on the first image data;

computing a second cross sectional moment of inertia based on the second image data;

computing a product of inertia based on the third image data; and computing the principal moments of inertia based on the first cross sectional area, the second cross sectional area, and the product of inertia.

70. The computer-readable medium of claim 67, wherein the first image data and the second image data comprise pixels indicating bone mineral density with precision errors less than about one percent.

71. The computer-readable medium of claim 67, wherein the first image data and the second image data comprise pixels spaced closer than about two pixels per millimeter.

72. The computer-readable medium of claim 67, wherein said step of computing principal moments of inertia further comprises computing a plurality of principal moments of inertia for the bone.

73. The computer-readable medium of claim 67, wherein execution of the one or more sequences of instructions further causes the one or more processors to perform the step of performing cone-beam reconstruction of the bone.

74. The computer-readable medium of claim 67, wherein:

execution of the one or more sequences of instructions further causes the one or more processors to perform the steps of determining a number of additional different angles of the plurality of projection angles for resolving principal moments of inertia at a particular position along a long axis of the bone, and receiving additional different image data, each comprising pixels indicating bone mineral density projected at a corresponding one of the additional different angles; and said step of computing the principal moments of inertia for the bone comprises computing the principal moments of inertia further based on the additional different image data.

75. A computer-readable medium carrying one or more sequences of instructions for deriving bone properties from images generated by a dual-energy x-ray absorptiometry apparatus having an x-ray source in fixed relation to an x-ray receiver, the source and the receiver moveably mounted to measure attenuation through a subject at a plurality of projection angles, wherein execution of the one or more sequences of instructions by one or more processors causes the one or more processors to perform the steps of:

receiving first data indicating a plurality of principal moments of inertia for a bone in the subject based on a plurality of images taken at the plurality of projection angles;

determining a stress on the bone associated with a particular scenario;

determining a probability of the particular scenario;

determining a risk of injury based on the probability of the particular scenario, the stress associated with the particular scenario, and the plurality of moments of inertia; and reporting the risk of injury for presentation to a human operator.

76. The computer-readable medium of claim 75, wherein the first data indicates the plurality of principal moments of inertia with precision errors less than about one percent.

77. The computer-readable medium of claim 75, wherein each image of the plurality of images comprises pixels spaced closer than about two pixels per millimeter.

78. The computer-readable medium of claim 75, said step of computing the risk of injury further comprising:

computing a strength modulus in a plane of the stress based on the plurality of principal moments of inertia; and determining a breakage of the bone based on the stress and the strength modulus.

* * * * *